(12) United States Patent
Blank et al.

(10) Patent No.: US 7,700,371 B2
(45) Date of Patent: Apr. 20, 2010

(54) METHOD FOR DETERMINING AN ANALYTE

(75) Inventors: Kerstin Blank, Munich (DE); Katrin Spinnler, Munich (DE); Thao Mai, Munich (DE); Filipp Oesterhelt, Wuppertal (DE); Ilka Gilbert, Munich (DE); Boris Steipe, Ontario (CA); Hermann Gaub, Neuhaus (DE); Christian Albrecht, Munich (DE); Gunnar Brink, Munich (DE)

(73) Assignee: Arrowhead Research Corporation, Pasadena, CA (US)

( * ) Notice: Subject to any disclaimer, the term of this patent is extended or adjusted under 35 U.S.C. 154(b) by 1363 days.

(21) Appl. No.: 10/479,249

(22) PCT Filed: May 31, 2002

(86) PCT No.: PCT/EP02/06003

§ 371 (c)(1),
(2), (4) Date: Dec. 28, 2004

(87) PCT Pub. No.: WO02/099423

PCT Pub. Date: Dec. 12, 2002

(65) Prior Publication Data

US 2005/0084855 A1    Apr. 21, 2005

(30) Foreign Application Priority Data

Jun. 1, 2001 (DE) ............... 101 26 798
Feb. 9, 2002 (DE) ............... 102 05 418

(51) Int. Cl.
*G01N 33/543* (2006.01)
(52) U.S. Cl. ............ 436/518; 436/524; 436/528; 436/535; 435/287.1; 435/287.2; 435/288.3; 435/288.4; 435/288.7; 422/50; 422/55; 422/57; 422/61; 422/68.1

(58) Field of Classification Search ............... 436/518, 436/524, 528, 535; 435/287.1, 287.2, 288.3, 435/288.4, 288.7; 422/50, 55, 57, 61, 68.1
See application file for complete search history.

(56) References Cited

U.S. PATENT DOCUMENTS 4,826,759 A * 5/1989 Guire et al. ............... 435/4

(Continued)

FOREIGN PATENT DOCUMENTS

DE    198 08 884 A1    9/1999

(Continued)

OTHER PUBLICATIONS

Vincent T. Moy et al., "Intermolecular Forces and Energies Between Ligands and Receptors", Science, Oct. 14, 1994, pp. 257-259, vol. 266.

(Continued)

*Primary Examiner*—Melanie J. Yu
(74) *Attorney, Agent, or Firm*—Sterne, Kessler, Goldstein & Fox P.L.L.C.

(57) ABSTRACT

The present invention relates to a method for determining an analyte in a sample. According to the method of the present invention, a probe is transferred from a stamp member onto an analyte that is bound to a support member. The present invention is particularly suitable for microarrays.

21 Claims, 22 Drawing Sheets

A

B

U.S. PATENT DOCUMENTS

| | | | |
|---|---|---|---|
| 4,966,839 A | | 10/1990 | Kaspar |
| 5,445,970 A | | 8/1995 | Rohr |
| 5,552,288 A | * | 9/1996 | Christensen et al. ......... 435/7.9 |
| 5,620,857 A | | 4/1997 | Weetall et al. |
| 5,726,913 A | | 3/1998 | Grimsrud |
| 5,861,954 A | | 1/1999 | Israelachvili |
| 5,866,328 A | | 2/1999 | Bensimon et al. |
| 5,871,918 A | | 2/1999 | Thorp et al. |
| 5,922,537 A | * | 7/1999 | Ewart et al. .................... 435/6 |
| 5,958,701 A | * | 9/1999 | Green et al. .................... 435/6 |
| 5,968,745 A | | 10/1999 | Thorp et al. |
| 5,992,226 A | | 11/1999 | Green et al. |
| 6,000,030 A | | 12/1999 | Steinberg et al. |
| 6,051,372 A | | 4/2000 | Bayerl et al. |
| 6,066,448 A | * | 5/2000 | Wohlstadter et al. ........... 435/6 |
| 6,086,821 A | | 7/2000 | Lee |
| 6,094,971 A | | 8/2000 | Edwards et al. |
| 6,096,386 A | | 8/2000 | Biebuyck et al. |
| 6,127,127 A | | 10/2000 | Eckhardt et al. |
| 6,132,971 A | | 10/2000 | Thorp et al. |
| 6,180,346 B1 | | 1/2001 | Thorp et al. |
| 6,180,418 B1 | | 1/2001 | Lee |
| 6,342,353 B1 | | 1/2002 | Heslot et al. |
| 6,346,387 B1 | | 2/2002 | Stewart et al. |
| 6,361,951 B1 | | 3/2002 | Thorp et al. |
| 6,387,625 B1 | | 5/2002 | Eckhardt et al. |
| 6,468,752 B1 | | 10/2002 | Bertling |
| 6,537,499 B1 | | 3/2003 | Bernard et al. |
| 6,537,749 B2 | | 3/2003 | Kuimelis et al. |
| 6,574,332 B1 | | 6/2003 | Moore et al. |
| 6,589,727 B1 | | 7/2003 | Klenerman et al. |
| 7,027,163 B2 | * | 4/2006 | Angeley ...................... 356/521 |
| 7,118,921 B1 | * | 10/2006 | Brennan et al. ............. 436/518 |
| 2002/0037530 A1 | | 3/2002 | Stewart et al. |
| 2002/0106683 A1 | | 8/2002 | Thorp et al. |
| 2002/0182597 A1 | | 12/2002 | Kuimelis et al. |
| 2003/0143616 A1 | | 7/2003 | Kuimelis et al. |
| 2003/0194697 A1 | | 10/2003 | Klenerman et al. |
| 2004/0086883 A1 | | 5/2004 | Gaub et al. |
| 2004/0241738 A1 | | 12/2004 | Stewart et al. |

FOREIGN PATENT DOCUMENTS

| | | |
|---|---|---|
| EP | 0 818 744 A2 | 1/1998 |
| EP | 0962 759 B1 | 8/2003 |
| WO | WO 93/19371 A1 | 9/1993 |
| WO | WO 99/36577 A1 | 7/1999 |
| WO | WO 00/58724 A1 | 10/2000 |
| WO | WO 02/14862 A3 | 2/2002 |
| WO | WO 03/066896 A2 | 8/2003 |

OTHER PUBLICATIONS

Blank, K., et al., "A force-based protein biochip," *PNAS* *100*(20):11356-11360, The National Academy of Sciences (2003).

Florin, E.-L., et al., "Adhesion Forces Between Individual Ligand-Receptor Pairs," *Science 264*:415-417, American Association for the Advancement of Science (1994).

Schwesinger, F., et al., "Unbinding forces of single antibody-antigen complexes correlate with their thermal dissociation rates," *PNAS* *97*(18):9972-9977, The National Academy of Sciences (2000).

Albrecht, C. et al., "DNA: A programmable force sensor," *Science 301*: (2003) American Association for the Advancement of Science, pp. 367-370.

Noy, A. et al., "Stretching and breaking duplex DNA by chemical force microscopy," *Chemistry & Biology 4*: (1997) Current Biology Ltd., pp. 519-527.

Strunz, T. et al., "Dynamic force spectroscopy of single DNA molecules," *Proc. Natl. Acad. Sci. 96*: (1999) The National Academy of Sciences, pp. 11277-11282.

* cited by examiner

Binding the Analyte

Legend for Figures 1-4:

Sample mixture (eg. cell lysate)

Receptors (eg antibodies)

Label or Marker (eg. fluorescent)

Probes (eg. Antibodies)

Support member (eg. glass)

Support member with binding area („Spot")

Probe-Analyte-Complex established

Sensor-Complex comprising first binding partner and second binding partner

A

B

① Euray-Slide

② PDMS

③ First Reference Complex - Oligo

④ Probe: Second Reference Complex - Oligo, Cy3-labelled (Unzipoligo)

⑤ Sample-Oligo (biotinylated)

⑥ Streptavidin

⑦ NHS-PEG$_{3400}$-Biotin

⑧ Methoxy PEG$_{2000}$ for blocking

Support member (PDMS) after Stamping:

Surface passivated with Methoxy-PEG

Surface coated with NHS-PEG$_{2000}$-Biotin + Streptavidin

1     Anti-Biotin-Antibody
2     Anti-Digoxygenin-Antibody
3     Streptavidin
4     Anti-Antitrypsin-Antibody
5     Biotin/Digoxygenin
6     Cy3
7     First Reference Complex-Oligo
8     Unzip-Oligo (second reference complex-Oligo, Cy3-marked)
9     Glasslide (here: Stamp)
10    PDMS (here: Support)
11    Sensor complex

| | |
|---|---|
| 1 | PDMS |
| 2 | Unzip-Complex with marker |
| 3 | Streptavidin |
| 4 | Biotinylated second antibody |
| 5 | Monoclonal antibody |
| 6 | Antigen |
| 7 | Glass slide |

1     PDMS
2     Unzip-Complex with marker at Unzip-Oligo
3     Streptavidin
4     Biotinylated second antibody
5     Monoclonal antibody
6     Antigen
7     Glass slide

| | |
|---|---|
| 1 | PDMS |
| 2 | Unzip-Complex with marker at Unzip-Oligo |
| 3 | Streptavidin |
| 4 | Biotinylated second antibody |
| 5 | Sample molecule (Antibody) |
| 6 | Antigen |
| 7 | Glass slide |

| 1 | PDMS |
| 2 | Unzip-Complex with marker |
| 3 | Streptavidin |
| 4 | Biotinylated monoclonal antibody |
| 5 | Antigen |
| 6 | Monoclonal antibody |
| 7 | Glass slide |

SEQUENCE LISTING

```
<160> NUMBER OF SEQ ID NOS: 4

<210> SEQ ID NO 1
<211> LENGTH: 50
<212> TYPE: DNA
<213> ORGANISM: Artificial Sequence
<220> FEATURE:
```

-continued

```
<223> OTHER INFORMATION: Description of Artificial Sequence: Synthetic
      Oligonucleotide

<400> SEQUENCE: 1
atacgccgta aagccggaga cagataagac gctacatgaa aaaaaaaaaa                50

<210> SEQ ID NO 2
<211> LENGTH: 50
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 2
atacgccgta aagccggaga cagataagac gctacatgaa aaaaaaaaaa                50

<210> SEQ ID NO 3
<211> LENGTH: 50
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 3
atacgccgta aagccggaga cagataagac gctacatgaa aaaaaaaaaa                50

<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 4
aaaaaaaaaa tctccggctt tacggcgtat                                     30
```

METHOD FOR DETERMINING AN ANALYTE

This application is a 371 of PCT/EP02/06003, filed May 31, 2002, which claims priority to German Patent Application No. 102 05 418.5, filed Feb. 9, 2002, and German Patent Application No. 101 26 798.3, filed Jun. 1, 2001. The entire contents of each of the above-identified applications are hereby incorporated by reference.

The present invention relates to a method for determining analytes and for qualitative and/or quantitative detection of analytes in a sample, in particular assays in the form of highly parallelized protein arrays.

There are many assays in existence for detecting substances in samples or for determining their concentration. According to one such method, specific antibodies are immobilized on a surface, and the sample composition is brought into contact with the antibody-decorated surface; it is then determined how much of the sample substance to be detected has bound to the surface. There are basically two different ways of detecting analytes. Either a marker is applied directly to the entire sample composition, or secondary marking is performed using a molecule that specifically recognizes the sample substance to be detected.

One important development of ligand assays involved the introduction of highly parallel microarrays of nucleic acids or proteins or other molecules serving as receptors. An overview is provided in Ekins, Clinical Chemistry, 1998, Vol. 44:9, 2015-2030. A protein array, for example, differs from conventional immune tests by virtue of its high parallelization of single detections, as well as the concomitant miniaturization and shorter average test duration. The array comprises a plurality of different receptors (antibodies, peptides, other scaffold proteins, DNA, RNA, RNA aptamers, etc.) that are each immobilized on a single, small area, these areas being distributed in an array on the surface. If a sample composition is applied to the array, specific binding of the sample molecules to the respective receptors occurs.

The binding of sample molecules to different areas can be detected directly or indirectly. In the case of direct detection, the sample molecule is marked in some way. Examples include the covalent binding of fluorophores, labeling of sample composition with radioactive isotopes or, in the case of aptamer chips, staining all the protein substance bound to the surface with Coomassie Blue or silver staining. One major disadvantage of such methods is the fact that all the substances contained in the sample, i.e. the substances for detection as well as other substances, are marked, which means that every non-specifically bound substance, or substance adsorbed on the surface, adds to the background noise of the read-out signal.

In the case of indirect detection, a second (secondary) receptor, referred to here as a probe, is directed at the sample substance specifically bound to the immobilized (primary) receptor. This is also referred to as the "sandwich format". The probe is marked with fluorophores or radioactivity, for example, or a reporter enzyme is attached (ELISA microarray). Only the substance within a composition that is actually being sought is marked. The signal-to-background ratio of the read-out signal is thus a considerable improvement on the direct marking technique. However, the problem of non-specific binding arises here as well, because it is not possible to distinguish whether the probe was bound specifically or adsorbed non-specifically.

The probe may be selective for a particular protein, or may bind an epitope that is common to all sample molecules. One example of a non-selective probe is an anti-His-tag antibody. This type of probe is used when the sample molecules are recombinant proteins from a cDNA bank that were fused with a His tag. For an example, see Büssow et al. Nucleic Acids Research, 1998, Vol. 26, No. 21, 5007- 5008. Another example is the ELISA "one sided assay", in which proteins are bound as receptors to the support member, and specific antibodies for these proteins are to be detected in the sample composition. The antibodies bound to the proteins are then marked using secondary antibody-enzyme complexes which bind specifically to the unchanging domains of the bound antibodies. The enzyme then produces a dye or a fluorophore that emits the actual signal for detection (see: Joos et al. Electrophoresis, 2000, Vol. 21, 2641-2650).

Non-selective indirect marking cannot be used, however, in cases where the sample substances do not have a common epitope, for example when detecting any non-recombinant proteins. In such a case, each sample molecule for determination must be detected with a selective probe specific to that molecule.

In order to increase the specificity of a detection test, selective probes for indirect marking may be used.

An important advantage of using selective probes for indirect marking is that the specificity of the test as a whole is enhanced. Sample substances bound non-specifically to the receptors, i.e. ligands that belong to other receptors, are not marked by the selective probe. When selective marking is performed, it is necessary to have exactly as many probes as there are receptors in the array. This gives rise to a number of problems, however:

The relative concentration of probes belonging to a certain ligand or receptor declines with increasing quantity of probes used, while the quantity of probes that cannot bind specifically yet contribute to the background signal through adsorption and/or non-specific binding increases.

Non-specific sample substances, i.e. substances which are bound elsewhere instead of to their specific receptor, and are therefore in the wrong place, are marked in just the same way as those which are specifically bound, because each probe is present in every single receptor area. This leads to "false-positive" results.

Markers are also applied to sample substance that is adsorbed somewhere on the surface, instead of at its specific site. This, too, can lead to false-positive results.

Furthermore, for each ligand it is necessary to have a predefined minimum concentration of probe for the given affinity of the probe, under which the concentration must not fall. Owing to the high degree of parallelization and the large number of different probes this entails, the total concentration of the probes increases as well. However, an increase in probe concentration leads in turn to a greatly increased background signal due to adsorption and non-specific binding to each single receptor area.

Another source of interference that is becoming increasingly important with high parallelization of detection and a greater number of substances to be detected on a chip is cross-reactivity. As the number of analytes for detection and their respective receptors increases, so, too, does the probability that a probe will react with other analytes besides those for which it is intended, or that analytes latch onto different receptors besides those to which they belong.

The various non-specific interactions and the adsorption of analytes and probes gives rise to a strong background signal and hence also a low ratio of signal to background, and therefore leads to unfavorable conditions for detection, with the result that molecules present in low concentrations can no longer be detected. This leads to "false-negative" results.

Another interference factor due to unwanted cross-reactivity and non-specific binding is that "false-positive" determinations can be obtained because of unwanted substances in the sample binding to receptor molecules.

To overcome this problem, it has already been proposed that the separate reactions be carried out on a protein chip in separate wells, so that the various reagent solutions and receptors, or ligands and probes, are unable to mix. However, such a test setup is too complicated to be of practical interest.

One assay using a microarray is described in WO 97/43447, for example. For the purpose of the assay, a plurality of wells that can be filled via transfer elements are arranged on a chip. By this means, it is possible for a plurality of wells on a chip to be filled simultaneously with many different reagents or samples. With the help of a kind of plunger, it is also possible to arrange a large number of substances on a surface that has a predetermined pattern. A reagent can then be applied to the transfer elements with a small roller. In this way, the separate substrates can react with a reagent on the chip itself. However, dosing substances into single wells is very complex. Furthermore, substances may be displaced by the roller, for example, or by other transfer elements, thus causing substrates to be contaminated.

From EP-A 0 865 323, it is also known how to produce a chip with which biological molecules can be adsorbed or immobilized on a surface in the right orientation. To do this, the molecules are transferred from one surface to another surface using a stamp means and substances that bind specifically to the molecules, such that they then have the right orientation on the surface to which they are transferred. The chips on which the molecules are present in the correct orientation can then be used to conduct the usual tests.

EP-A 09 62 759 describes a method for measuring binding forces that is based on the deformation of an elastic plunger. The plunger coated with a sample substance is brought into contact with a surface coated with a probe. When the plunger is dissociated from the surface, it is possible to measure separation forces that can serve to identify the analyte. This method is suitable for measuring forces between single molecules, but not for parallelized tests in which binding forces acting on many molecules are to be determined or compared simultaneously. In the method described in EP-A 09 62 759, co-operative effects are to be expected, i.e. the events are not independent of the number of bindings that are subjected simultaneously to tensile force.

A method using an AFM is described in U.S. Pat. No. 5,992,226. Here, instead of being bound on a flat surface, as is common practice in AFM measurements, a sample is bound between a pointed projection and the AFM probe tip. This method, too, is not suitable for parallelizing the measurements.

The object of the present invention is to provide a method for determining one or preferably many analytes in a sample, and with which analytes can be detected with greater sensitivity. Another object is to provide a method that can be performed easily by the user and without complicated equipment, that does not require any special instruments with parts that are prone to failure, and can also be carried out by personnel who have not received special training.

This object is achieved with the method of the invention for determining an analyte in a sample. The method is characterized in that a composition or sample that might contain the analyte being determined is brought into contact with a first surface (i.e. a support) such that the analyte possibly contained in the sample is bound to said support member;

a second surface (i.e. a stamp), to which a probe that can bind the analyte is bound, is brought closer to the support member so that the probe and the analyte can interact, the binding of the probe to the analyte and the binding of the analyte to the support member being more stable under an externally applied tensile force than the binding of the probe to the stamp member;

the stamp member and support member are separated from each other; and it is determined whether the probe is bound to the support member and/or how much probe is bound to the support member.

Using the method according to the invention, it is possible to detect many different substances using a chip, whereby the sensitivity is increased relative to known methods, in that the local concentration of the substances that are supposed to react with each other is optimized at the respective "detection site", and the quantity of non-specific bindings that could interfere with detection is minimized. When the probe concentration rises, the problems of cross-reactivity and non-specific bindings that are incurred with other methods are avoided. This advantage increases still further with higher levels of parallelization.

In describing the present invention, some terms are used that will now be defined.

The term "analyte" refers to all types of molecules, substances or materials to be detected in a sample. Possible analytes are all molecules or complexes, be they organic, inorganic or with organic and inorganic constituents, that have at least two sites capable of binding specifically. In the present description, analytes are also referred to as "sample substances" or "sample molecules".

The term "determining" is used here for both qualitative and quantitative detection of an analyte, and can include determination of the amount and/or concentration of the analyte. The term also covers the identification and/or any characterization of an analyte on the basis of physical parameters.

In the context of the present invention, the term "receptor" is meant to designate any substance or any molecule that has a molecular detection site for an analyte and that can bind the analyte in a specific manner.

In the context of the present invention, the term "receptor" is meant to designate any substance or any molecule that has a molecular detection site for an analyte and that can bind the analyte in a specific manner, and that can also attach a marker to the analyte. A marker can be bound directly to the probe molecule, or the probe molecule can be joined to a further molecule, in particular to a sensor complex, preferably in such a way that the particular part of the sensor complex that may be dissociated is marked.

A "sensor complex" refers to a combination of at least two molecules that are able to bind with each other and can preferably bind specifically to each other, wherein the combination of molecules is chosen in such a way that the tensile force necessary to separate them is greater under the given experimental conditions than the tensile force necessary to separate molecules that are non-specifically bound, yet smaller than the tensile force necessary to separate the specifically bound analytes from their binding partner or for separating the immobilized, e.g. covalently bound receptors.

The method according to the invention is used to detect, qualitatively or quantitatively, one or preferably a plurality of analytes in a sample. The sample or composition that may contain the analyte or analytes to be determined—also called the sample substance—can be of various kinds. It will usually consist of solutions or suspensions. Lysed cells or cell homogenates, or tissue extracts can be used. The sample substance to be analyzed can also be body fluids such as blood, urine, liquor, lymph fluid, etc. The composition can be diluted, and suitable buffer substances/solutions or salts can be added. There are no particular limitations regarding the ionic strength and the pH value of the composition, the values of which are preferably in a range that does not significantly impair the binding of the sample or the analyte to the probe. Preferred pH ranges are from 1 to 13, more preferred is a range from 3 to 11, and most preferred is a range from 4 to 10. The composition may contain a single analyte, but usually two or more different analytes for determination are contained in the composition or sample. One advantage of the method according to the invention is that a plurality of different analytes can be determined simultaneously.

There are no particular restrictions on the type of analyte to be determined. Analytes can be molecules, molecular groups, ions or complexes. They can be monomers, dimers or polymers. The analytes will usually be organic compounds, preferably biomolecules or biopolymers, whereby small molecules are also conceivable. Preferred analytes are proteins, peptides, nucleic acids, carbohydrates, lipids or metal compounds and other biopolymers. These analytes may exhibit modifications, in particular chemical modifications. It is also possible that different kinds of molecules are bound to each other. It is also conceivable that compounds which do not occur naturally, or fragments thereof, are bound to one of the biological molecules. The method according to the invention is particularly suitable for samples containing a plurality of analytes, e.g. body fluids, in which different kinds of molecules and molecular complexes are to be detected.

Most preferably, the analyte or analytes for determination are proteins, polypeptides or peptides, and nucleic acids. These may be naturally occurring molecules, as well as fragments, analogs, conjugates and/or derivatives thereof. The proteins, polypeptides or peptides may originate from a natural source or be manufactured as recombinants or be chemically synthesized. They can be present in native or in non-native form, for example as denatured molecules. The proteins, polypeptides or peptides may exhibit post-translational modifications, and they can be glycosylated, phosphorylated, acylated and/or amidated. They can include a "tag", for example a peptide sequence that is recognized as an antibody epitope. Known tag sequences are 6×His-tag, FLAG-tag, myc-tag, HA-tag, etc. Other tags are known to the person skilled in the art. Non-peptidic tags may also be contained in the analytes. Proteins as analytes may comprise a number of subunits, and may be homooligomers or heterooligomers comprised of polypeptide subunits.

In order to perform the method according to the invention, the analyte or analytes to be determined in a sample are brought into contact with two binding partners that are able to bind specifically to the respective analytes, whereby one of the binding partners is immobilized or immobilizable on a first surface while the other binding partner is immobilized or immobilizable on a second surface. There is broad scope for varying the selection and immobilization of the binding partners, as well as their immobilization site. When the expressions "analyte" and/or "analytes" are used in the following, they refer in each case to both a singular and a plurality of substances for detection, unless explicitly defined otherwise.

A binding partner (receptor or probe) is immobilized on a first surface referred to in the following for the sake of simplicity as a "support member" or "support", without this necessarily specifying that said surface is the lower layer. The surface termed the support can equally form the upper layer when performing the method. The second surface is referred to for the sake of simplicity as the "stamp member" or "stamp".

The materials of which the two surfaces (support member and stamp member) consist may be identical or different, and either or both surfaces may be coated in a suitable manner. What is preferred is either one surface made of a rigid material and the other formed of an elastic material, or both surfaces are made of elastic material so that they can adapt precisely to each other when brought into contact, and hence that optimal contact between the binding partners is possible. The support member and/or the stamp member may be made, for example, of glass, polydimethyl siloxane (PDMS), nylon, polystyrene or other plastics. It is preferred that at least one of the two surfaces is produced from an elastic material, preferably an elastic plastic material. It is particularly preferred that at least one surface is made of a siloxane, in particular polydimethyl siloxane. Various other flexible materials or mixtures thereof are possible. Another possible material is polyacrylamide gel, the elastic properties of which can be adapted to experimental requirements by varying the molecular weight and the degree of cross-linking. The surface may be composed of a single material, a mixture of materials, or a system of elements made of one or different materials.

Functional groups may be present on the surfaces or can be added later. One example, inter alia, is to use glass with a derivatized surface in order to provide binding groups for immobilizing a binding partner. One example of the latter is silanized glass.

The surfaces on which the binding partners are immobilized may have a geometry of some kind that allows them to be brought into contact. In one preferred embodiment, both the support member and the stamp member form plane surface areas of equal size. In another embodiment, the surface has a three-dimensional structure, e.g. is configured as a cylinder, roller, etc. To perform the method according to the invention, all that is important is that both surfaces have corresponding sub-areas, or have congruent sub-areas to which binding partners are respectively bound, and that a tensile force can be exerted on the surfaces. It is also possible, therefore, to use particles at the nanometer or micrometer scale, e.g. micro- or nanoparticles.

In order to minimize non-specific interactions of the analytes and probes with the support member, the surface of the support member and/or the stamp member may preferably be passivated in an known manner by binding protein substances or polymers, and, particularly preferably, by coating with polyethylene glycol.

At least one of the two surfaces, generally the stamp member, has mechanical properties that enable good contact over the entire area of the other surface, usually the support member. The term "good contact" includes the correct gap between the support member and the stamp member to ensure that the bound analytes and probes can be close enough to each other for them to be able to interact, while also ensuring that they are not damaged by the exertion of mechanical pressure. It must also be ensured that contact with the support member is substantially uniform over the entire surface of the stamp member.

The stamp member may be composed of a single material, a mixture of materials or a system of elements made of one or different materials. Particularly good results are obtained when the surface of the stamp member and/or the support member has an array of wells, because these facilitate the distribution of the fluid. Said wells can also help to separate sub-areas carrying different receptors and probes.

The method according to the invention can be performed by immobilizing or binding the analyte(s) directly to the support member. In most cases, it is less appropriate to immobilize by adhesion, because then all the molecules of a sample will be bound to the surface, with adverse effects on sensitivity. However, non-specific adhesion may be considered for samples that do not contain any other immobilizable molecules besides the analyte. The analyte can also be bound to the surface directly via functional groups. However, the latter embodiment should be preferably used only when the substance for detection has a functional group that distinguishes it from substances present in the sample. Another option is to provide the surface of the support member where binding is to occur with spacer molecules or groups of spacers that perform functions for binding the analyte or analytes. Such spacer molecules or bridge molecules are known to the person skilled in the art and do not need to be elucidated here. All molecules that can bind to the support member and which can provide a functional group for binding the analyte are suitable for use.

In one preferred embodiment of the present invention, however, receptors which can bind the analytes specifically are immobilized on one of the two surfaces, preferably the support member. The receptors can be immobilized by covalent or non-covalent binding, by binding directly on the surface, or via bridge molecules. Binding via a specifically binding pair is equally possible.

In the context of the present invention, the term "receptors" refers to substances that can participate in a specific binding with a molecule, i.e. which are capable of molecular recognition and/or have a group that can be recognized by another binding partner. Receptors, therefore, are usually partners within a specifically binding pair, the other partner being the analyte for determination. A highly diversified range of bindable partners can be considered for the specifically bindable pairs of which one partner is used as a receptor in accordance with the invention, whereby the specificity of binding can relate not only to a particular partner, such as antibodies with affinities to certain antigens, or biotin-avidin/Streptavidin, but also to a group or class of bindings, such as antibody-protein A. Examples of specifically binding partners include: antibodies, peptides, other scaffold proteins, DNA, RNA, RNA aptamers and hence the pairs antigen-antibody, haptene-antibody, anti-idiotype-antibody-antibody, DNA-DNA, RNA-RNA, DNA-RNA, RNA aptamer-peptide, receptor-ligand, lectin-sugar, zinc-finger protein-DNA, enzyme-substrate, biotin-avidin/Streptavidin, etc., as well as their respective derivatives or analogs. Other fragments capable of binding can be used instead of antibodies, and nucleic acid derivatives and the like can also be used instead of DNA or RNA.

In one preferred embodiment, the binding pairs used are comprised of an antibody and a substance with an epitope recognized by the antibody, such as an antigen, haptene or anti-idiotype-antibody. In the present description of the invention, the term "antibody" refers also to antibody fragments or antibody derivatives, as well as functional fragments of antibodies or derivatives thereof that can recognize and bind to the epitope. The antibodies can be polyclonal or monoclonal antibodies, although monoclonal antibodies are preferred. Known fragments and derivatives are Fv-, Fab-, Fab'- or F(ab')$_2$ fragments, "single-chain antibody fragments", bispecific antibodies, chimeric antibodies, humanized antibodies and fragments containing CDRs (complementarity determining regions) that recognize an epitope of the analyte.

Depending of the type of analyte to be detected, the receptor can be composed of antigens or haptenes, as well as antibodies or their derivatives or fragments.

In another preferred embodiment, the partners used for the specifically binding pair are nucleic acids such as DNA (deoxyribonucleic acid) or RNA (ribonucleic acid), synthetic nucleic acids such as LNA (locked nucleic acid) and PNA (peptide nucleic acid), and three-dimensional structures made of nucleic acids, preferably aptamers.

According to the present invention, it is preferred that the sample molecules or analytes do not bind directly to the support member, but via molecules that are immobilized on the support member. In one embodiment, for example, the receptor can be biotinylated and be bound via a Streptavidin molecule to the support member, which is similarly biotinylated. If the receptor is an antibody, said antibody can be chemically activated by oxidizing certain groups of the glycosylations to form aldehyde groups. Said aldehyde groups, in turn, can bind amino groups or hydrazide groups of a modified surface (see: Solomon et al. Journal of Chromatography, 1990, Vol. 510, 321-329). Another method with which the person skilled in the art is familiar is to conjugate amino groups of the antibody with carboxy groups of a surface by using ethyl-(dimethylamino)-carbodiimid/N-hydroxy-succinimide.

The method according to the invention is particularly advantageous when not just one analyte is to be detected in a sample, but several analytes simultaneously and in parallel. This is done by providing at least two and preferably more sub-areas on the support member and/or the second surface deployed in accordance with the invention, with said sub-areas carrying the different respective receptors and/or probes. Antibodies, fragments or derivatives thereof, for example, or different antigens or even different aptamers or nucleic acid moieties or derivatives thereof can be used in this way as receptors and/or probes, whereby one such sub-area can be provided for one particular kind of receptor or probe, i.e. that receptors and/or probes each with specificity for one analyte are present in each sub-area, whereby different sub-areas carry receptors and/or probes with specificity for different analytes, namely on defined, delineated areas of the support member and/or the stamp member. The sub-areas can also be further sub-divided into smaller areas that can each have a separate function, or can support different receptors or probes. An area can thus be sub-divided into a plurality of areas that are all capable of binding the same analyte, whereby one area is configured as a control area, empty area or for standardization, whereas the other areas serve to determine an analyte. Several areas can also carry the same kind of receptor or probe in each case. Such areas are referred to as "spots". A support member can hold up to 10,000 spots/cm$^2$. The term "microarray" is also used for such an arrangement. By using a highly parallel arrangement of receptors or probes with differing specificities, e.g. antibodies or antigens, many different analytes contained in a particular sample composition can be captured and bound specifically to the respective spots on the support member.

In one preferred embodiment of the method according to the invention, at least one of the two surfaces, i.e. either the support member or the stamp member, has sub-areas that each carry different binding partners capable of binding to different analytes. It is particularly preferred that both the support member and the stamp member each have sub-areas that are capable of binding with different analytes, whereby corresponding sub-areas, or sub-areas of the support member and the stamp member facing each other can bind to different binding sites of the same analyte. In this way, it is possible with one such apparatus to detect many different analytes in a single test run. This saves time and expense.

In another embodiment, at least one sub-area of the support member or the stamp member is sub-divided into a plurality of spots. In one embodiment, the spots are then loaded with receptors in such a way that at least one spot can serve as a control for the "correct" contact between stamp member and support member, while the remaining spots each carry the same or different receptors capable of binding with the analyte to be detected. As a means of control, receptors capable of binding directly with the probe can be immobilized on a spot so that binding occurs in any event even when no analyte is present, and the marker is transferred to the receptor if the contact was sufficient. This type of control enables false-negative results due to inadequate contact between the surfaces to be recognized and avoided.

In another variant, at least one spot can have a combination of receptor and the analyte for detection, as a kind of internal standard, in order to ensure that the test bindings permit a binding of the analyte to the probe and that the binding of analyte to receptor does not break prematurely.

In another variant, the arrangement of receptors and probes can be varied, even when the spots are facing each other, in such a way that there are spots with receptors and spots with probes present both on the support member and on the stamp member. The type and arrangement of the receptors and probes is freely selectable and can be optimized for each test and each analyte.

In yet another variant of the invention, spots with different receptors or probes capable of binding with an analyte are provided on a sub-area. This has the advantage that a useful signal can still be obtained even when molecules may be present in different states and can then bind with different binding partners or with different binding strengths. This embodiment is also suitable for optionally differentiating between different states of an analyte. It may also be useful in such a case to consider different sensor complexes with different binding strengths for the probes capable of binding with an analyte, in order to have further options for differentiation.

Probes that can bind specifically to the analyte are bound to the second surface, generally the stamp member.

In one embodiment of the present invention, when all analytes to be detected have a binding site that is common to all, e.g. a group, or the unchanging part of an antibody, only one type of probe capable of binding with the common binding site can be bound to the stamp members. In another embodiment, the stamp member has sub-areas that carry different probes, whereby the probes are each capable of binding to different analytes.

The probe, in turn, is a partner of a specifically binding pair, the other partner being the analyte to be detected. Suitable binding pairs are the same pairs as those described above for receptor-analyte pairs. Of course, the receptor and the probe must bind to different sites on the analyte. For this reason, the analyte must provide at least two binding sites. For the person skilled in the art, it can clearly be seen that, as far as possible, no binding site may be sterically hindered by the binding on the other binding site, i.e. that both binding sites should be sterically arranged in such a way that they are available for the respective other binding partner regardless of whether a binding site is already occupied.

The probe usually binds selectively to the analyte, and is specific for a particular analyte. The probe is preferably an antibody, a fragment or a derivative thereof. The variants of antibody, fragments and derivatives thereof that are described above with reference to the receptors for the sample or the analyte, as well as nucleic acids, are similarly conceivable as probes. The probe usually contains a marker. Said marker can be detected by a detection device. The marker is preferably a fluorescence dye such as fluoresceinisothiocyanate (FITC), fluorescein, rhodamine, tetramethyl-rhodamin-5-(and-6)-isothiocyanate (TRITC), Texas Red, cyanine dye (CY3 or CY5), etc. Fluorescence dyes are advantageous because they can be detected in very small quantities. The marker is generally bound covalently to the probe. Other marker options are reporter enzymes (ELISA) or the use of radioactive isotopes.

What is important for the present invention is that the binding of the probe to the analyte and the binding of the analyte to the support member or to the receptor under an externally applied tensile force is more stable than the binding of the probe to the stamp member, or the binding of the two binding partners of the sensor complex to each other.

The support member or the stamp member is brought into contact with the sample containing the analyte for detection until a sufficiently high efficiency of the binding of analyte to receptors or probes is achieved with minimum possible non-specific adsorption. This is usually achieved by incubating the support member with the sample. The support member (or the stamp member) is then removed from the incubation solution, washed to remove surplus substances, if necessary, and dried, if so required.

The stamp member with the probe is brought closer to the support member that has the analyte molecules for detection bound to its receptors, in such a way that the probe and the analyte interact and are able, in specific cases, to bind together. The stamp member and the support member are then separated, and it is determined whether the probe and/or how much probe is bound to the support member. By binding the probes to a second surface, the present invention ensures that, when the two surfaces are close together, the maximum possible concentration of probes is present for marking the analyte. In addition, the differential force test ensures that the probe is essentially transferred only when the analyte is actually present.

One advantage of the method according to the invention consists in the fact that an increase in the local concentration of reaction partners occurs at two sites in the detection chain; binding of the analyte to a spatially limited area ("spot") leads to an increase in the local concentration of the analyte relative to the concentration in solution, and binding of the corresponding probes to a spatially limited area of the second surface corresponds to an increase in the local concentration of probes compared to the probes being added as a solution and with high purity, because the amount of associated material is not increased, and the other probes are sorted out. This leads to an improved signal-to-noise ratio and hence to improved sensitivity and a lower detection limit. This advantage operates above all when there is strong parallelization.

In order to detect how much probe has been transferred from the stamp member to the support member by binding to the analyte, the probe preferably carries a marker, or is bound to a marker. Possible markers (also called labels) for the method according to the invention include all analytically detectable groups or substances. Within the context of the invention, marking refers to a detectable property by which some binding partners differ from others. Physically determinable parameters are preferably used for this purpose. Potential markers include, in particular, any atoms or groups that are radioactive or which cause a change in optical or electrical properties. All reporter groups known to the person skilled in the art are suitable for this purpose. Examples are radioactive markers such as 3H, 14C, 32P, 35S, fluorescent, luminescent, chromophore groupings or dyes, metals or conducting groups, or substrates of enzymes or reporter enzymes. Preferably, fluorescent or chromophoric groups are used as markers. When proteins are used as binding partners, one option is to apply Coomassie Blue or silver staining to the protein substance bound to the surface.

The marker is preferably a fluorescence dye such as fluoresceinisothiocyanate (FITC), fluorescein, rhodamine, tetramethyl-rhodamin-5-(and-6)-isothiocyanate (TRITC), Texas Red, cyanine dye (CY3 or CY5), etc. Fluorescence dyes are advantageous because they can be detected in very small quantities. Markers are generally bound either directly to the probe or to that portion of the sensor complex that is transferred.

For each specifically binding pair, it is also possible to use several markers, and different markers can also be used for different probes or for probes capable of binding to different analytes.

A preferred technical realization of the invention is one in which the probe is not bound directly to the stamp member material, but via a sensor complex formed by two binding partners. The stamp member is bound fixedly to a first binding partner, and the probe is bound fixedly to a second binding partner. The first binding partner may be bound covalently to the stamp member, while the second binding partner may be bound covalently to the probe. The first and the second binding partner may bind specifically or non-specifically to each other, whereby the binding is usually non-covalent. The binding of the probe to the analyte and the binding of the analyte to the support member is more stable under an externally applied tensile force than the binding of the first binding partner to the second binding partner.

In this case, the marker is preferably carried by that portion of the sensor complex which is transferred, and not by the probe itself. It is particularly preferred to use two complementary nucleic acid strands to immobilize the probe. For the method according to the invention, it is now advantageous if binding occurs in such a way that the bindings can be "unzipped" when a tensile force is applied to the hybridized strands. In this embodiment, the binding partner, preferably the probe, is bound to the complementary strand in such a way that they are unzipped when a tensile force is applied. This is achieved in the following way: When the immobilized first strand is fixed to the surface with its 3' end, and with the 5' end remaining unattached, the binding partner is bound to the complementary second strand at the 5' end such that, when tractive force is applied to the binding partner, the force acts on the 5' end of the complementary second strand and is thus applied only to one base pair that can be dissociated one after the other, with the strands being separated like a zip fastener being undone. This type of pairing is referred to as "unzip pairing". If the binding partner is bound in this case to the 3' end, the force necessary to separate the strands is much greater because it acts simultaneously on all the base pairs. When the immobilized first strand is immobilized with the 5' end, the binding partner must be bounded to the binding partner at the 3' end of the second strand in order to unzip the strands.

In a special embodiment, the first binding partner is a naturally occurring or synthetic nucleic acid whose 5' end is bound to the stamp member. The second binding partner is a natural or synthetic nucleic acid that can hybridize with the first binding partner and form a nucleic acid duplex. In this embodiment, the 3' end of the second binding partner is bounded to the probe. A reverse arrangement is similarly possible, namely that the 3' end of the first binding partner is bound to the stamp member, and the 5' end of the second binding partner is bound to the probe.

In a further embodiment, the probe is the 3' end of the second binding partner or, in the reverse arrangement, the 5' end of the second binding partner.

Hence, the probe is bound to the stamp member via interaction of the nucleic acid duplex. If the stamp member is now brought closer to the support member, the probe reacts with the analytes in the sample. If the stamp member and the support member are subsequently separated from each other, the binding between the first binding partner and the second binding partner is dissociated. The force required to dissociate said binding is relatively small, since the nucleic acid duplex is pulled apart like a zip fastener. While the binding energy and hence the binding affinity increases with the length of the nucleic acid duplex, the force required to unzip the nucleic acid duplex remains constant. The high binding affinity between the nucleic acid strands ensures that the complex does not unbind unless an external force is applied to it, and that the probe cannot freely dissociate and therefore remains bound to the stamp member as long as it has not interacted with the analyte specifically bound to the support member.

The binding partner should be bound to the complementary nucleic acid strands in such a manner that neither the hybridization of the complementary nucleic acid strands nor the binding of the binding partner to the other partner is sterically hindered.

In a further embodiment, a binding partner is a polypeptide to the C-terminal end of which a nucleic acids is covalently coupled. Bindings of this kind can be produced using, for example the method disclosed in WO 01/04265. The method operates with mRNA molecules that are modified with a puromycin tag and which bind to the C-terminal of their polypeptide after they were expressed in vitro.

Options for immobilizing nucleic acid strands are known to the person skilled in the art and do not need to be elucidated here.

One advantage of nucleic acid duplexes as sensor complexes for "suspending" or immobilizing the probe is that the high binding affinity between the nucleic acid strands ensures that the complex is not dissociated prematurely from the surface unless an interaction between the partners of the specifically binding pair was possible, and/or unless an external force was applied. Another advantage is that, by varying the bases, in particular the GC content, and also if the pair is not an unzip pair, the length of the duplex and the unbinding force of the duplex can be adjusted with precision. The person skilled in the art is aware that, in addition to the A, T, G, C and U bases, other bases such as inosin, for example, or synthetic nucleic acids such as PNA and/or LNA can be used, and hence that the unbinding force can be varied still further. The unbinding force can also be varied by modifying bases. In this way, the person skilled in the art is able to "fine-tune" the unbinding force.

It is usually not necessary to know the exact unbinding forces of the sensor complex and the binding of the specifically binding partners. It generally suffices to know the order of magnitude when there is a considerable difference between the unbinding forces of the two complexes. For example, the unbinding force between an antigen and antibody is generally much greater than the force necessary to "unzip" a nucleic acid duplex in the manner described above.

In cases where the unbinding forces are to be set very precisely, it is possible to measure directly the unbinding force between two molecules by using a force microscope. This technique has been described in detail in various scientific publications. Unbinding forces of antibody-antigen complexes range between 50 pN and 150 pN (Schwesinger et al., PNAS, 2000, Vol. 97, 18, 9972-9977); in order to "unzip" a nucleic acid duplex, 9±3 pN need to be applied to a pure A/T sequence and 20±3 pN in the case of a pure C/G sequence (Rief et al., Nature structural biology, 1999, Vol. 6, 4, 346-349). In contrast, to separate a nucleic acid duplex by applying a force to the 5' end of the first and the 5' end of the second strand, or to the 3' ends, it is necessary to apply between 30 and 150 pN, depending on the number of base pairs involved. A particularly stable binding under external application of force is the binding between biotin and avidin. To dissociate this binding, 160±20 pN must be applied (Florin et al., Science, 1994, Vol. 264, 415-417).

Another possible implementation is to have the probe bound to the stamp member surface via only one binder. Said binder may be bound covalently to the probe. The binder binds non-specifically directly to the stamp member surface. The binding of the probe to the analyte and the binding of the analyte to the support member is more stable under an externally applied tensile force than the binding of the first binding partner to the stamp member.

The first binding partner preferably has a high affinity or a low rate of dissociation to the second binding partner, or the binder has a high affinity or a low dissociation rate to the stamp member surface. This prevents the probe going freely into solution and dissociating from the stamp member. A high affinity or a low dissociation rate with simultaneously low stability under an externally applied tensile force can be achieved by varying the binding distance of the binding of the first binding partner to the second binding partner, or of the binder to the surface. If the binding distance is greater for the same activation energy for separation, the force sufficient to dissociate the binding decreases. Under an externally applied tensile force, the binding of a sample substance which binds non-specifically to a receptor or is adsorbed to the support member is usually weaker than the specific binding to a receptor. This means that the stability of the probe/stamp member binding under an externally applied tensile force can be adjusted in such a way that it is greater than the binding of a sample substance bound non-specifically to a receptor or adsorbed to the support member, but weaker than the specific binding of the probe to the sample substance, and weaker than the binding of the sample substance to the receptor. This has the advantage that, when the probe interacts with a non-specifically bound or adsorbed sample substance, the probe is not bound to the support member, but remains bound to the stamp member. In conventional methods in which the solution containing the marked probe is incubated with the support member, the probe also binds to the support member when it binds to sample substances that are non-specifically bound, thus leading to a higher background signal. This can be avoided with the present invention.

According to the invention, it is preferred that the first binding partner and the second binding partner are natural or synthetic nucleic acids, preferably single-strand DNA and/or single-strand RNA and/or single-strand LNA and/or single-strand PNA.

In a further embodiment in which the probe is bound to the stamp member surface only by a binder, said binder preferably consists of a polymer that interacts with the surface of the stamp member. The polymer is preferably a biopolymer, a polyamino acid or a polysugar, that mediates the interaction with the support member via charged, hydrophobic or polar side groups.

According to the method of the invention, it is preferred that the stamp member comprises a plurality of areas separated from each other, in which probes with different specificity for different sample molecules are bound. The support member is configured thereby in the form of a microarray, preferably in the form of a protein microarray. The stamp member is brought into contact with the microarray or analyte, the probes being moved in such a way that they cover the binding surface of the corresponding analyte or corresponding receptor. Sample molecules that are bound will thus interact with the probe. In conventional techniques in which the probes are applied to the support member as a mixture in solution, any probe can interact with the bound sample substances on any binding surface. The sample substance is marked regardless of whether it is bound specifically or non-specifically, or whether it is merely adsorbed on the surface. This can be avoided with the present invention. Since the probes are brought to bear in such a way that they cover only the binding surface of the corresponding analyte or corresponding receptor, the corresponding analyte is detected there and only there. All other sample substances that are bound there non-specifically or adsorbed on the surface are not marked. This type of direct addressing by a probe of the sample molecules that belong to it also prevents any cross-reaction of the probe with other sample molecules or receptors. Therefore, at any predetermined location only one type of analyte is bound and marked. The advantages of direct addressing are that the molecules are present in enriched, very pure form without interference from associated materials that might otherwise disrupt the test.

Microarrays can be produced using methods that are essentially known. Cf. on this point McBeath et al., Science, 2000, Vol. 289, 1760-1763, or Lueking et al. Analytical Biochemistry, 1999, Vol. 270, 103-111. The methods described in WO 00/27521 and EP 0 865 323 are also suitable for producing microarrays. The probe bound to the support member is similarly detected by detecting the marker using methods known from the prior art. For example, fluorescence markers are detected by scanning with a standard fluorescence scanner.

The probe serves in particular to mark the analyte immobilized on the support member. A special aspect of the invention is that the probe is guided locally to the site where its associated analyte is bound. The advantage here is that the probe does not enter freely into solution. This is preferably done by binding the probe to a stamp member with low force but high affinity. The stamp member is brought into contact with the analyte array, the probe being moved in such a way that it covers the binding surface of the corresponding analyte. Sample substances bound to a receptor will thus interact with the corresponding probe as well.

If the stamp member is now separated from the support member, the binding of the probe to the stamp member is dissociated, the probe remains on the analyte array and thus marks the analyte specific to it. If, when the stamp member contacts the support member, the probe does not find a sample molecule to which it specifically binds, it will remain no the stamp member. Following the series of steps as described above ensures that only those sample molecules are marked with a probe that have bound specifically to a probe. All sample molecules that bound non-specifically to the support member remain unmarked and therefore do not contribute to the background signal.

It is important for the preferred embodiment of the method according to the invention that receptors are immobilized on the support member which are able to bind specifically to the analyte to be detected, and that probes are immobilized on the stamp member which are similarly capable of specific binding with the analyte, whereby the probes are immobilized via a sensor complex. When determination of the analyte is carried out, the support member is first brought into contact with the sample, for example, so that the analyte can bind to its respective receptor. The stamp member is then brought into contact with the support member in such a way that the probe can similarly bind to the analyte. The probe, in turn, is bound via a sensor complex to the stamp member. Therefore, if the analyte to be detected is present in the sample and has bound to its assigned receptor and the associated probe when the support member and stamp member have been brought into contact, there is a chaining of the receptor, the analyte, the probe and the sensor complex, whereby the sensor complex and the receptor are each bound firmly to their respective surface. If the two surfaces are now separated from each other, a tensile force is exercised on this chain that leads to the unbinding of the weakest binding in the chain. Therefore, if the binding between the two binding partners in the sensor complex is selected so that it is weaker than the binding of the analyte to the receptor and the probe, but stronger than a non-specific binding of the analyte or probe to a surface or a non-specific binding partner, the sensor complex will then dissociate when the tensile force is applied if the analyte has bound to its correct receptor and to the correct probe, whereas the sensor complex will remain intact if non-specific binding has occurred between the probe and the support member, or if a non-specific analyte has been bound by the probe. Since the binding partner of the sensor complex that is not bound to the stamp member carries the marker, the marker is transferred in the first case to the support member, whereas in the second case the marker remains bound to the stamp member. After the surfaces have been separated, it can therefore be established whether marker has been transferred to the support member or how much marker has been transferred. The proportion of marker transferred to the support member is a measure for the type and quantity of analyte present in the sample, since only if an analyte is bound is it possible for the sensor complex to unbind and hence for marker to be transferred to the support member.

This embodiment of the invention may be performed in such a way that the probe is bound to the support member and the receptor to the stamp member, i.e. that the probe is immobilized via the sensor complex to the support member, that the support member with the probe immobilized via the sensor complex is brought into contact with the sample containing the analyte to be detected, whereby the analyte, if present in the solution, binds to the probe. In a further step, the stamp member is then brought closer to the support member such that an interaction is possible between the probe, any bound analytes and the receptor, and that the two surfaces are subsequently separated again. In this case, when the analyte has been bound at the correct site, applying the tensile force causes the sensor complex to be separated and the marker to be transferred onto the stamp member. Which embodiment is most suitable for the respective purpose can be easily established by the person skilled in the art by conducting routine experiments. To implement the method of the invention, it is irrelevant where the receptor and the probe are immobilized; all that is important is that the binding forces are selected such that the binding of the binding partners in the chain fulfil the condition defined above.

If the method of the invention is implemented according to the particularly preferred embodiment in such a way that a plurality of analytes in a sample are simultaneously detected, the support member and preferably the stamp member as well are configured in such a way that a corresponding number of sub-areas are provided that are each fitted or filled with the specific receptors or probes. In order to enhance the sensitivity and reliability of the test, it may be preferred to provide a plurality of sub-areas with the same receptor and to evaluate these sub-areas before averaging the measurement results. However, it is also possible to provide only one sub-area for each particular analyte.

In an alternative embodiment of the method according to the invention, sub-areas may also be provided on the support member and the stamp member that are equal in number and are positioned opposite each other, whereby, for example, four sub-areas are provided on one of the two surfaces to provide the respective binding partner for the same analyte, while on the corresponding sub-area facing it on the other surface, two or four different binding partners for the same analyte are provided in order to increase the reliability of determination still further. For example, a plurality of sub-areas can be provided with probes for the same analyte, whereby the probes of the individual sub-areas differ in the type of marker, with the result that different types of marker are used, for example, or that different molecules of a particular marker type are used.

In a further variant, it is also possible to provide, on the support member and the stamp member, at least two sub-areas that each bind to the same analyte, whereby one sub-area carries receptors and the other carries probes, so that, for the same analyte, there are receptors arranged on the support member as well as the respective probes. This, too, serves to increase the reliability of the test and to avoid false-positive or false-negative results.

The present invention also relates to an apparatus for determining an analyte in a sample. The apparatus according to the invention comprises a surface (i.e. a stamp member) to which a probe is bound that can bind to the analyte when brought into contact with it, the binding of the probe to the analyte being more stable under an externally applied tensile force than the binding of the probe to the stamp member; The preferred embodiments of the apparatus according to the invention correspond to the preferred embodiments of the method according to the invention and were explained in the foregoing.

Preferably, a first binding partner is bound fixedly to the stamp member and a second binding partner is bound fixedly to the probe, wherein the first binding partner and the second binding partner can bind non-covalently to each other. Preferably, the first binding partner and the second binding partner are nucleic acids such as DNA and/or RNA.

In one preferred embodiment, the first binding partner is a nucleic acid the 5' end of which is bound to the stamp member, while the second binding partner is also a nucleic acid, whereby the 3' end of the second binding partner is bound to the probe. Equally, the 3' end of the first binding partner can be bound to the stamp member, while the 5' end of the second binding partner can be bound to the probe.

It is preferred that the stamp member comprises a plurality of demarcated areas in which different probes with different specificities for different sample molecules are bound. The stamp member of said apparatus can then be brought closer to a corresponding support member on which different analytes are bound in the form of an array.

The apparatus can further comprise an additional surface (i.e. the support member) on which one or more analytes can be immobilized. It can also comprise a device for bringing closer and separating the support member and the stamp member, and/or a device for determining whether the probe is bound to the support member.

In one preferred embodiment, an apparatus is provided in accordance with the invention for qualitative and/or quantitative detection of an analyte in a sample, said apparatus comprising a support member and a stamp member that are so configured that they can be brought into contact with each other, wherein at least two sub-areas are provided on at least one of the two surfaces, and wherein the support member is provided with receptors, whereas the stamp member is provided with probes immobilized via a sensor complex, and wherein different sub-areas carry receptors and/or probes capable of binding to different analytes.

A sub-area can be structured as a plurality of spots, whereby said spots can each carry the same or different receptors and/or probes.

The present invention provides a method and an apparatus for determining one or more analytes in a sample and makes it possible to detect many analytes simultaneously with high specificity and sensitivity. By using two different binding partners capable of binding specifically to the analyte or analytes to be detected, one of said binding partners being bound via a sensor complex to a surface, it is possible to overcome the disadvantages of the prior art and to largely avoid non-specific signals. By this means, a reduction in the signal/background ratio is achieved, which leads to higher specificity and sensitivity.

With the present invention, a method is provided that can be performed more easily, with less complicated equipment and less expensively than prior art methods.

The invention can be deployed in a diversity of ways: Expression profiles of cells or tissues can be compared. For example, it is possible to compare the expression profiles of cancer cells and "normal" cells. Such comparisons can also be used for diagnostic purposes. It is also possible to analyze the influence of particular substances on cell expression. One possible use if mRNA profiling, for example.

Another important application is the detection of diseases. Certain body fluids can be analyzed using an array of different antibodies, whereby the presence and/or concentration of a specific antigen in the sample composition can provide an indication for a certain disease. Many findings can thus be obtained in a single experiment. Other possible applications are conceivable for the person skilled in the art.

Another object of the invention is therefore to use the apparatus defined above for the parallel determination of a plurality of parameters characteristic for a certain disease, or for parallel detection of a plurality of antigens or antibodies.

Another object of the invention is to use the method of the invention for parallel detection of a plurality of parameters specific to a disease, or of a plurality of antigens or antibodies in an assay.

In order to show clearly the advantages that can be achieved with the object of the invention, the successive steps of a detection method and the possibilities of different binding events will be explained in the following. The binding events may be based on different kinds of binding, whereby non-specific bindings in particular, e.g. due to adsorption, as well as specific bindings due to cross-specificity or cross-reactivity are unwanted, because they lead to false-positive and/or false-negative results, or to insensitive detection signals due to an increase in the background signal.

Depending on the type of detection system, the site of the detection reaction (such as the position on a chip) and the type of binding are of decisive importance for identifying the analyte.

In the prior art methods, unwanted bindings can occur in the first step, binding of the analyte, due to specific binding at a receptor that is not provided for the specific analyte, and in the second step, binding of the probe, due to binding to an analyte other than that for which the probe is intended, to the receptor intended for binding the analyte, due to non-specific adsorption of the probe, or due to cross-specific binding. According to the invention, these unwanted bindings are to be avoided, among other ways by more targeted addressing.

If one examines a common, multi-step detection method, one can distinguish between the following cases in the separate steps of the method:

| 1st step: binding of analyte A to receptor R: | |
|---|---|
| specifically, at the intended site: | A-sp |
| specifically, at the non-intended site (cross-specificity): | A-ksp |
| non-specifically, at the non-intended site: | A-unsp |
| 2. step: binding of probe S to the support plate/the bound analytes: | |
| specifically, at the intended site: | S-sp |
| specifically, at the non-intended site (cross-specificity): | S-ksp |
| non-specifically, at the non-intended site: | S-unsp |

This gives rise, therefore, to the following combination options:

| | |
|---|---|
| a) A sp - S sp | "correct-positive", desired |
| b) A sp - S ksp | false-positive |
| c) A sp - S unsp | false-positive, false-negative, increase in background signal |
| d) A ksp - S sp | false-positive, false-negative |
| e) A ksp - S ksp | false-positive, false-negative |
| f) A ksp - S unsp | false-positive, false-negativeM; increase in background signal |
| g) A unsp - S sp | Increase in background signal |
| h) A unsp - S ksp | Increase in background signal |
| i) A unsp - S unsp | Increase in background signal |

In the case of specific and sensitive detection methods, the only combination in the ideal scenario is the "A sp-S sp" one; all other combinations are less favorable, because they lead to false-positive (e.g. falsely marked analytes), false-negative (e.g. by receptor occupation, displacement of the analyte actually intended) or insensitive detection signals (by increase in the background signal).

The method of the present invention makes it possible to increase the portion of combinations pursuant to a) and to reduce or in preferred cases to largely avoid the portion of combinations b) to i). This enhances the reliability, the precision and the sensitivity of the test method compared to prior art methods.

Identification of the analyte is based on the site of the probe after the detection reaction, for example the position on the chip, under the assumption that the desired type of binding is present. Thus, all cases that contain at least one step that leads to unwanted bindings (be it in respect of the site and/or the type of binding) is disadvantageous (cases b to i above).

If the analyte specifically bound at the intended site is marked by a non-addressing probe that binds cross-specifically or non-specifically, a decrease in the concentration of the probe occurs that can adversely affect the detection limit for the actual analyte that is being detected. In addition, false-positive signals occur if the non-addressed probe binds cross-specifically or non-specifically, for example to other receptors. These cases b), e) and h) are avoided according to the invention by the fact that on appropriately prepared surfaces the non-specific binding is less stable under an externally applied force than a specific binding. In the method according to the invention, potential cross-specificity of probes to other analytes has no negative impacts, because the probes can reach only the intended site for binding due to the addressing system provided by the invention:

In methods known to date, a false-positive detection reaction can occur with non-addressed probes due to non-specific binding of the probe to the "free" receptor or to analytes bound incorrectly to the receptor, unless this can be eliminated in a cleaning step. Depending on the extent of non-specific binding—and only in the case of non-addressed probes, the probes can also lead to false-negative signals if they firstly block binding sites for the probes that are actually intended for those sites, and are subsequently removed in the cleaning step that follows. According to the invention, these cases c), f) and i) are avoided by the combination of direct addressing of the probe and use of the differential force test. When applying the method according to the invention, the probe reaches only sites where it is supposed to bind specifically, and it remains bound only on condition that the binding was made specifically to "its" analyte. If non-specific binding occurs, the probe is removed again by application of the differential force test. False-positive signals, false-negative signals and probe-induced increases in the background signal can thus be avoided. There is no adverse effect on the detection limit, either, because loss of probes and the concomitant reduction of probe concentration does not occur.

In prior art methods, non-addressed probes can also bind to the wrong site, which leads to an increase in the background signal and hence to a reduction of sensitivity and deterioration of the detection limit. The increase in background signal is therefore a crucial problem for cases g), h) and i). The problem of false-positive signals and increased background signal due to nonspecific binding of an analyte is solved by the present invention by means of direct addressing of the probes, combined with the differential force test.

If the analyte is bound to the wrong site due to cross-specificity, this leads to false-positive detection signals (where identification is via the non-addressed probe) or also to false-negative signals (where identification is via the site of the receptor, when the analyte actually intended is displaced and/or its binding sites are blocked).

If the analyte is non-specifically bound, then the background signal increases and the sensitivity and detection limit deteriorate. Detection of the analyte is also made more difficult by the fact that the loss of analyte can be relatively substantial at low analyte concentrations. This is particularly disadvantageous when non-addressed probes are used.

(A) On a support mfember there are three spots on each of which an antibody with a particular specificity is immobilized. After incubation with a sample composition, the antibody molecules of two spots are decorated with sample molecules, whereas the antibody molecule of the third spot has no binding because the sample composition did not contain the corresponding analyte. Sample molecules non-specifically bound are also located on the spots. At the top of the Figure, a stamp member is shown that has three complementary spots each bound to a first binding partner. Attached to the first binding partner is a second binding partner that is bound fixedly to a marked probe. The marked probes of each spot also have a certain specificity for the sample molecule. The stamp member surface is no disposed and brought closer to the support member in such a way that the marked probes can interact with the immobilized sample molecules.

(B) The stamp member and the support member are then separated from each other. The two spots on the left of the support member now contain sample molecules to which marked probes are bound, because the force necessary to unbind the probe from the analyte is greater than the force that was required to separate the first binding partner from the second binding partner. In the case of the third spot (on the right), the probe could not interact with a specifically bound analyte. For this reason, the complex comprising the first and second binding partners was not separated. In a further step it can now be determined whether the probes, and/or how many of the respective probes are bound to the corresponding spots on the support member.

The portrayals in FIGS. 1 to 4 and in FIGS. 5, 6, 8, 12, 13 and 17 are not to scale, in order to enhance their clarity. To provide a clearer view, only one antibody molecule is shown per spot.

Figure 1:
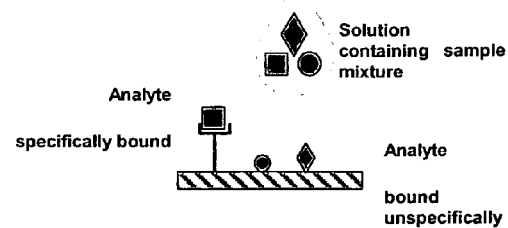
FIG. 1 illustrates the principle of a ligand assay in which a sample composition is brought into contact with a support member. In addition to specific binding to a receptor, non-specific binding of analytes to the support member also occurs. Below the Figure, a legend is provided for the symbols used; this legend applies to all the Figures.
Figure 1:
Figure 1:
Figure 1:
Figure 1:
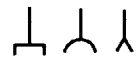
Figure 1:
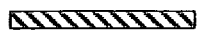
Figure 1:
Figure 1:
Figure 1:
Figure 2:
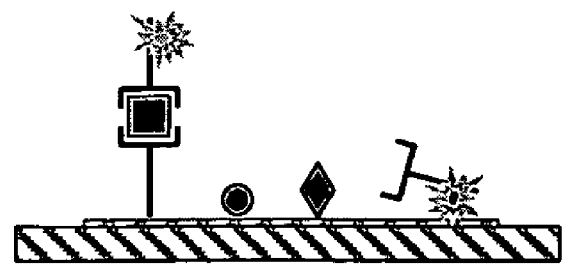
FIG. 2 shows a "spot" on a support member, with a market probe bound specifically to the analyte, non-specifically bound analytes and a non-specifically bound probe.
Figure 3:
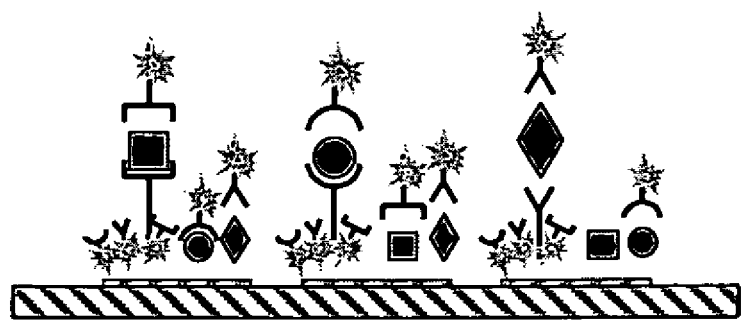
FIG. 3 shows a support member with three spots on a support member. Each spot carries an antibody that is specific for a sample molecule. By providing a plurality of spots, many different analytes and many different specifically marked probes cause a strong increase in the background signal. The background signal increases proportionally to the number of spots or probes.
Figure 4:
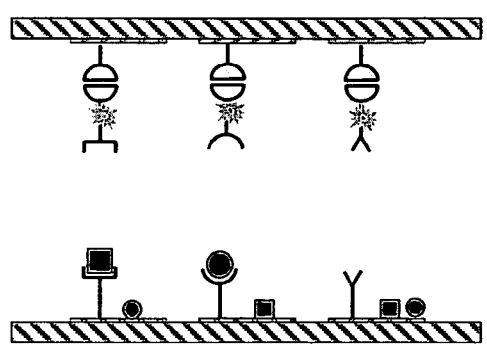
FIG. 4 shows in schematic form one embodiment of the method according to the invention.
Figure 4:
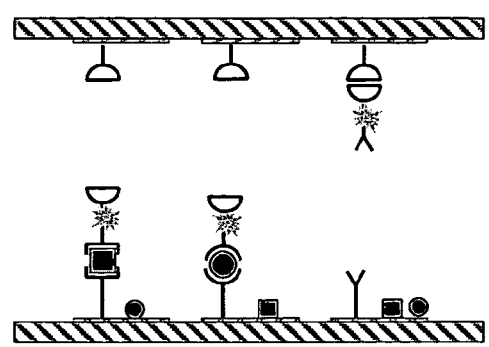
Figure 5:
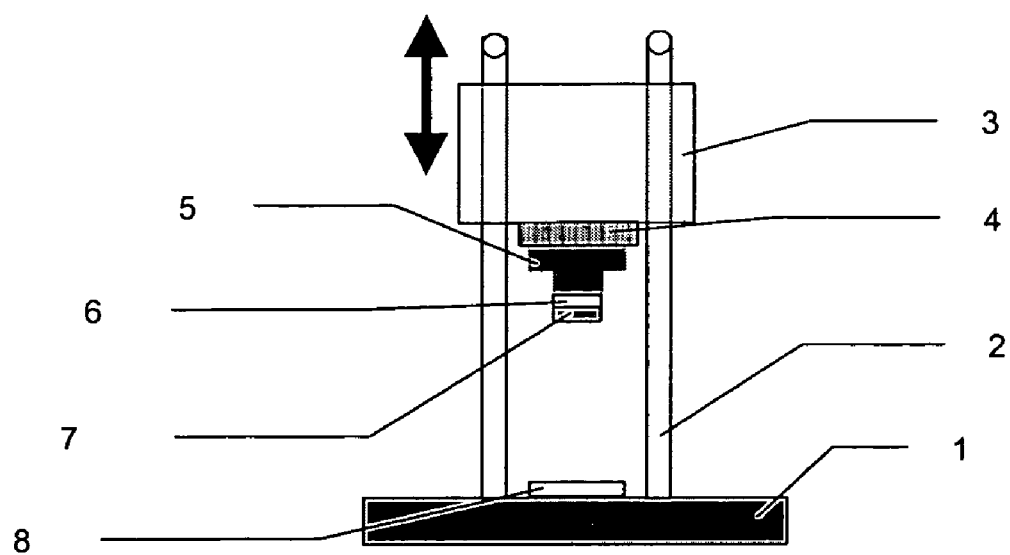

FIG. 5 shows a possible embodiment of a stamping apparatus that is suitable for implementing the method according to the invention. A more precise description of a possible embodiment is provided in the section headed "Implementation Methods".

Figure 6:
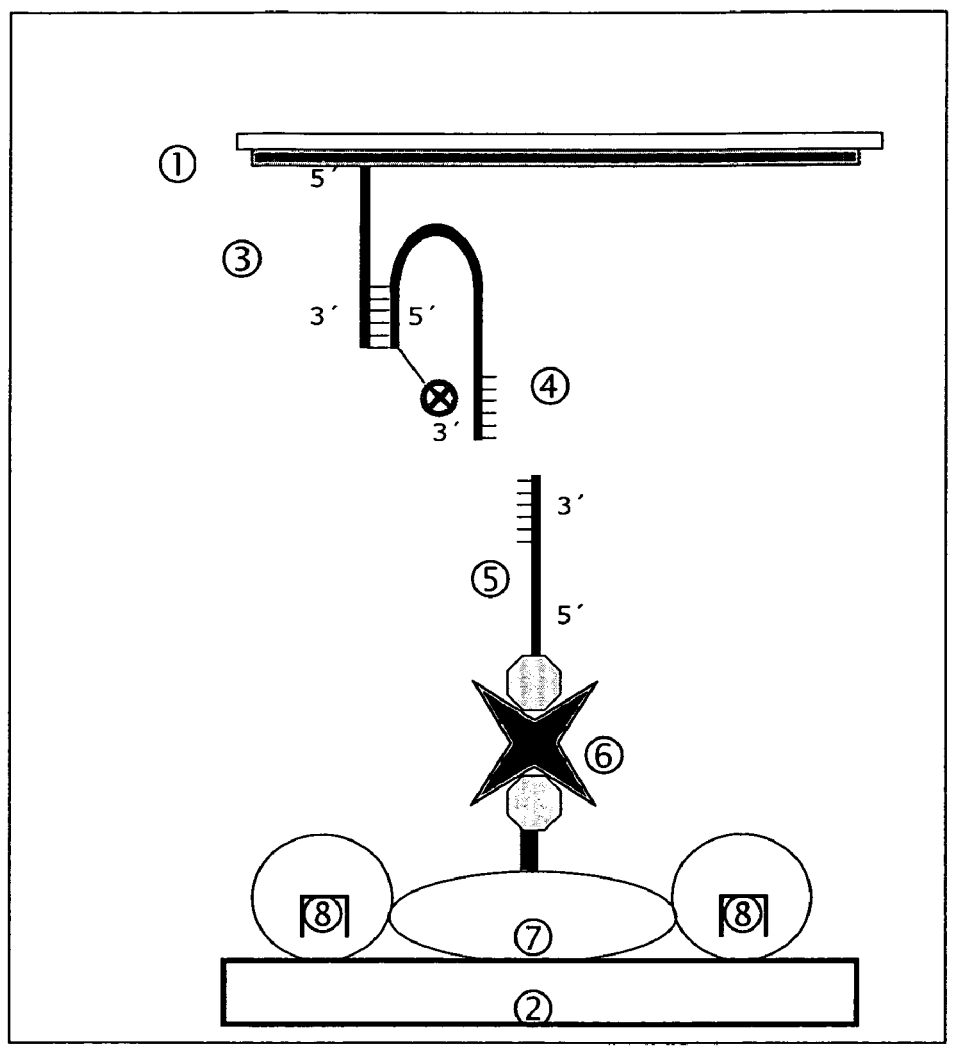

FIG. 6 shows the setup of experimental Example 3, in schematic form.

Figure 7:
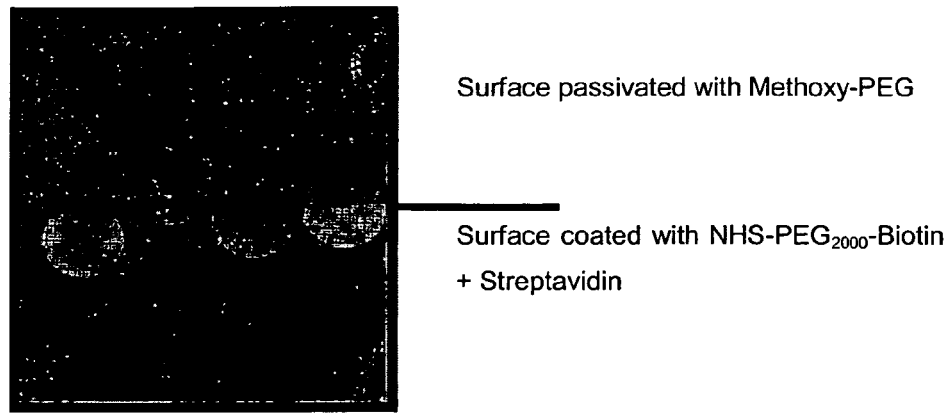

FIG. 7 shows an example of a fluorescence scan of a support member after stamping (cf. experimental Example 3)

Figure 8:
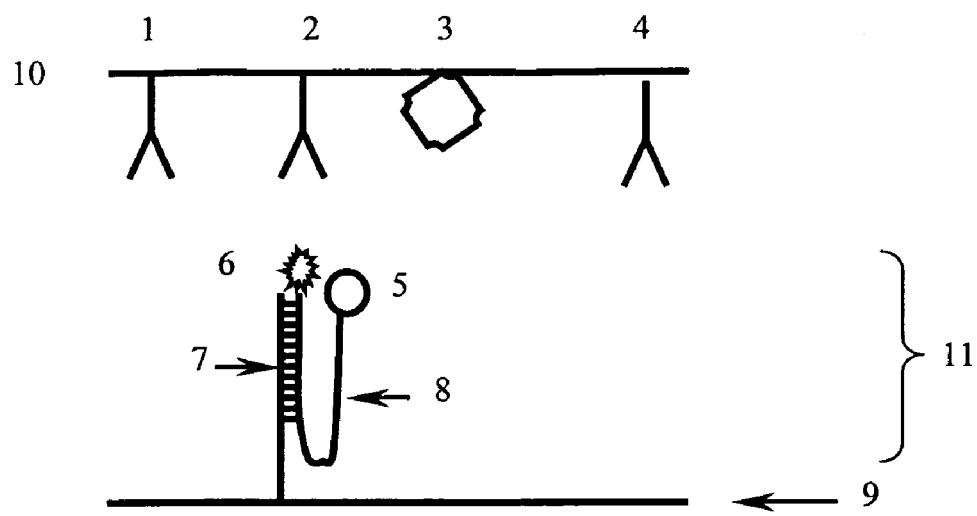

FIG. 8 shows the setup of experimental Example 4, in schematic form.

Figure 9:
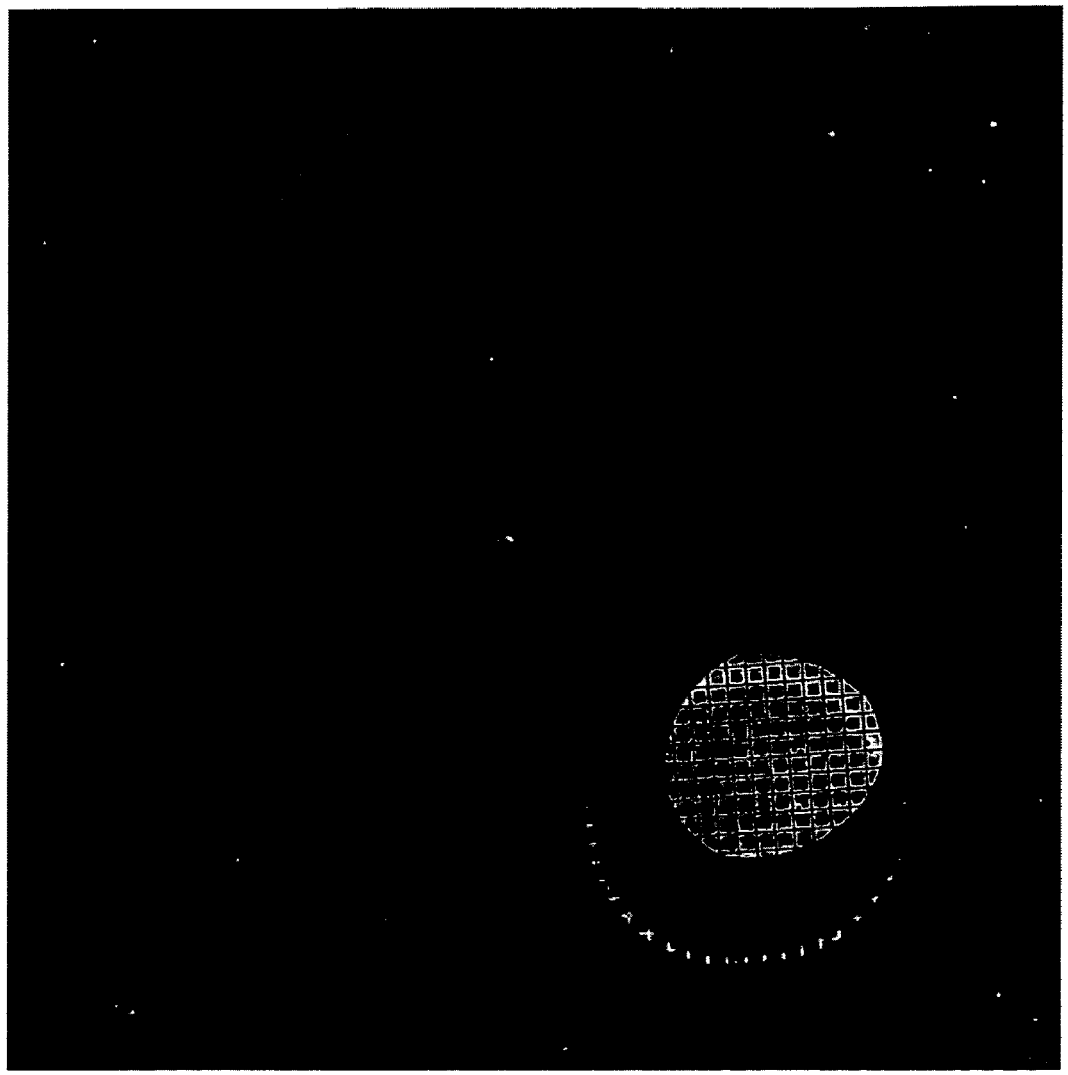

FIG. 9 shows an example of a fluorescence scan of a PDMS piece (here: support member) after stamping with unzip oligo-biotin. At top left, Streptavidin solution was linked; at top right, anti-digoxygenine; at bottom left, anti-antitrypsin; at bottom right, antibiotin. The light-colored patches are the antibiotin antibodies marked with unzip oligo or Streptavidin. Darker areas, showing non-specific transfer of anti-digoxygenin and anti-antitrypsin antibodies, can also be seen.

Figure 10:
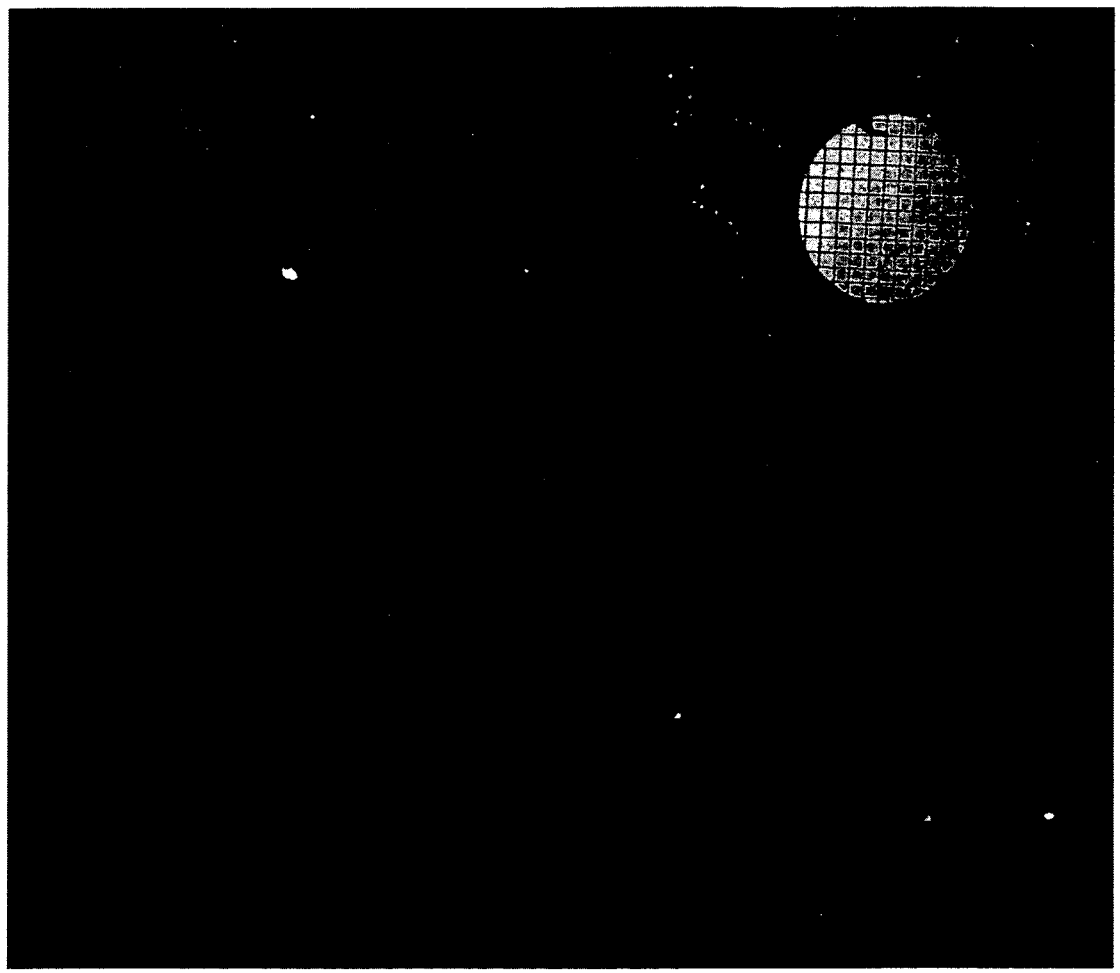

FIG. 10 shows an example of a fluorescence scan of a PDMS piece (here: support member) after stamping with unzip oligo-digoxygenin. At top left, Streptavidin was bound; at top right, anti-digoxygenine; at bottom left, anti-antitrypsin; at bottom right, antibiotin. The only light-colored area is where anti-digoxygenin antibody was immobilized; all other spots are very weak.

Figure 11:
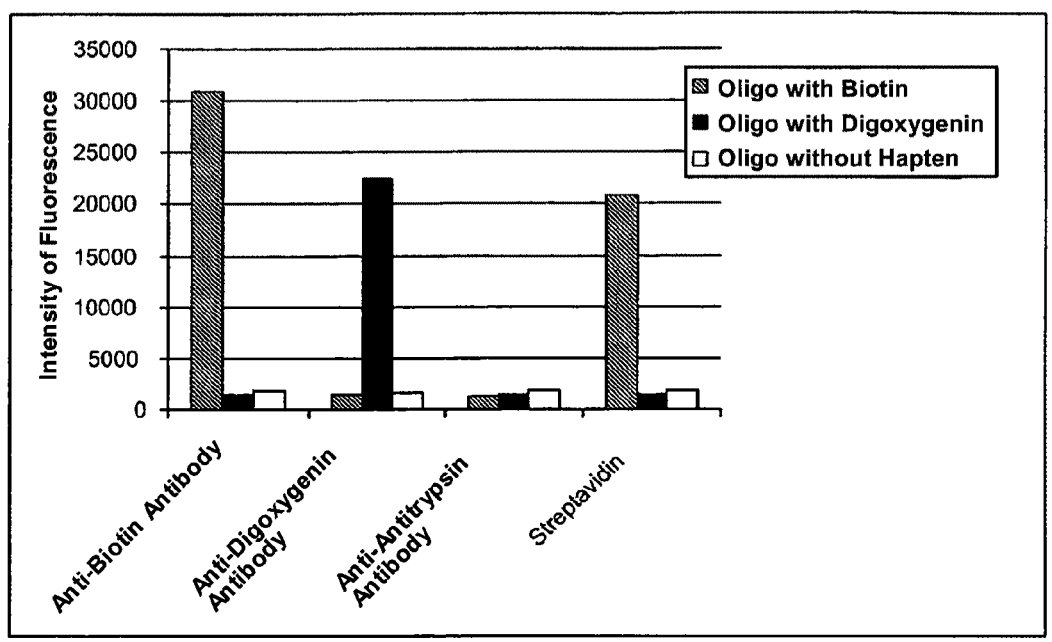

FIG. 11 shows a diagram summarizing the results of experimental Example 4: stamping an unzip oligo with and without haptenes on surfaces that were coated with four different proteins (antibiotin, anti-digoxygenin, anti-antitrypsin antibody, Streptavidin)

Figure 12:
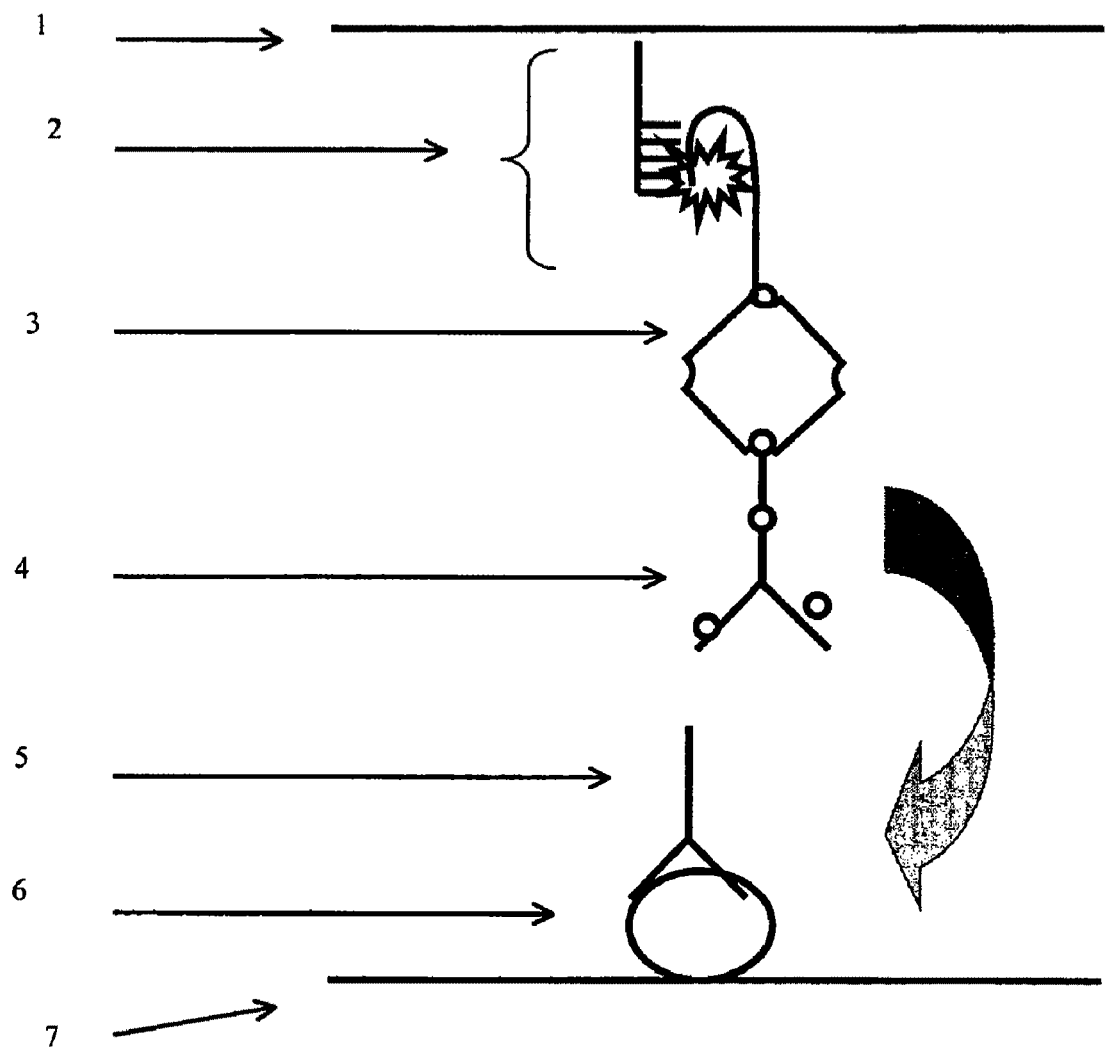

FIG. 12 shows the general schematic setup of experimental Example 6.

Figure 13:
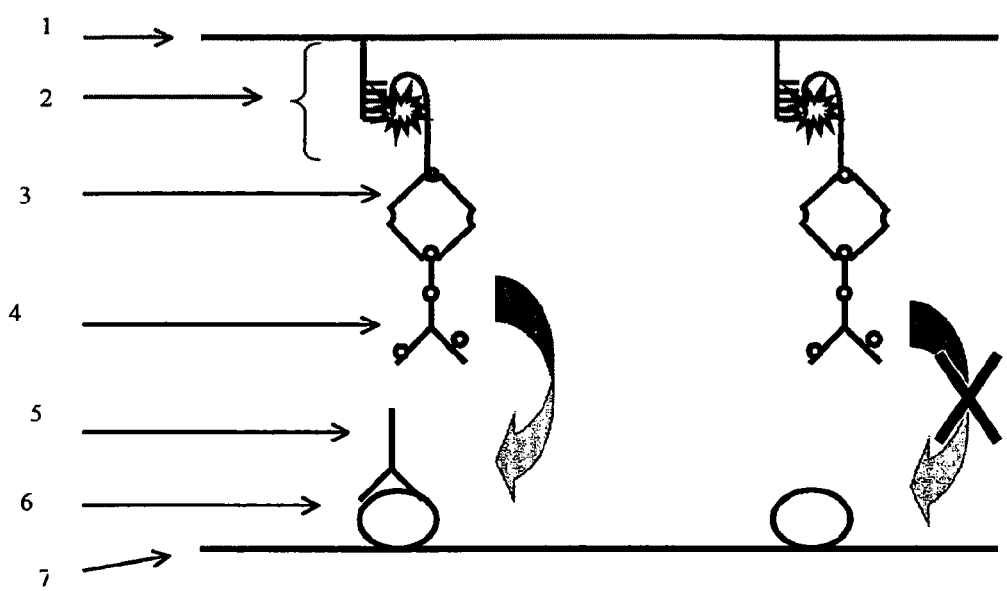

FIG. 13 shows in schematic form the setup of experimental Example 6, first arrangement.

Figure 14:
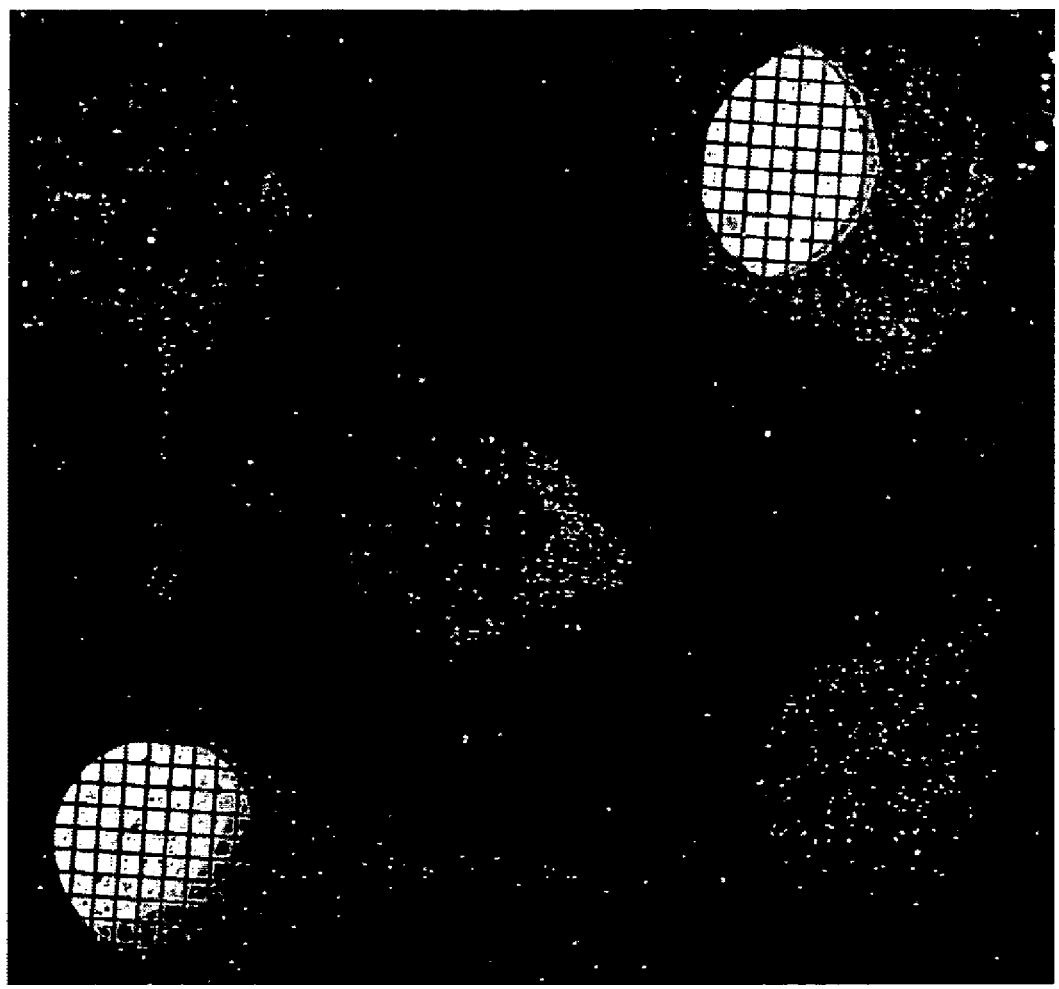

FIG. 14 shows transfers of fluorescence marker to the support member when the sample solution contained the antibodies anti-β-galactosidase and anti-Interferonγ. At top left, Troponin T was bound to the support member; at top right β-galactosidase; at bottom left, Interferonγ; at bottom right α1-antitrypsin. The light-colored areas can be found where the unzip oligo marked the bound anti-β-galactosidase or anti-Interferonγ antibodies. Darker areas of non-specific transfer to the support member, where the sensor complex was stamped directly onto receptors not carrying analytes, or onto the passivation (center), can also be seen.

Figure 15:
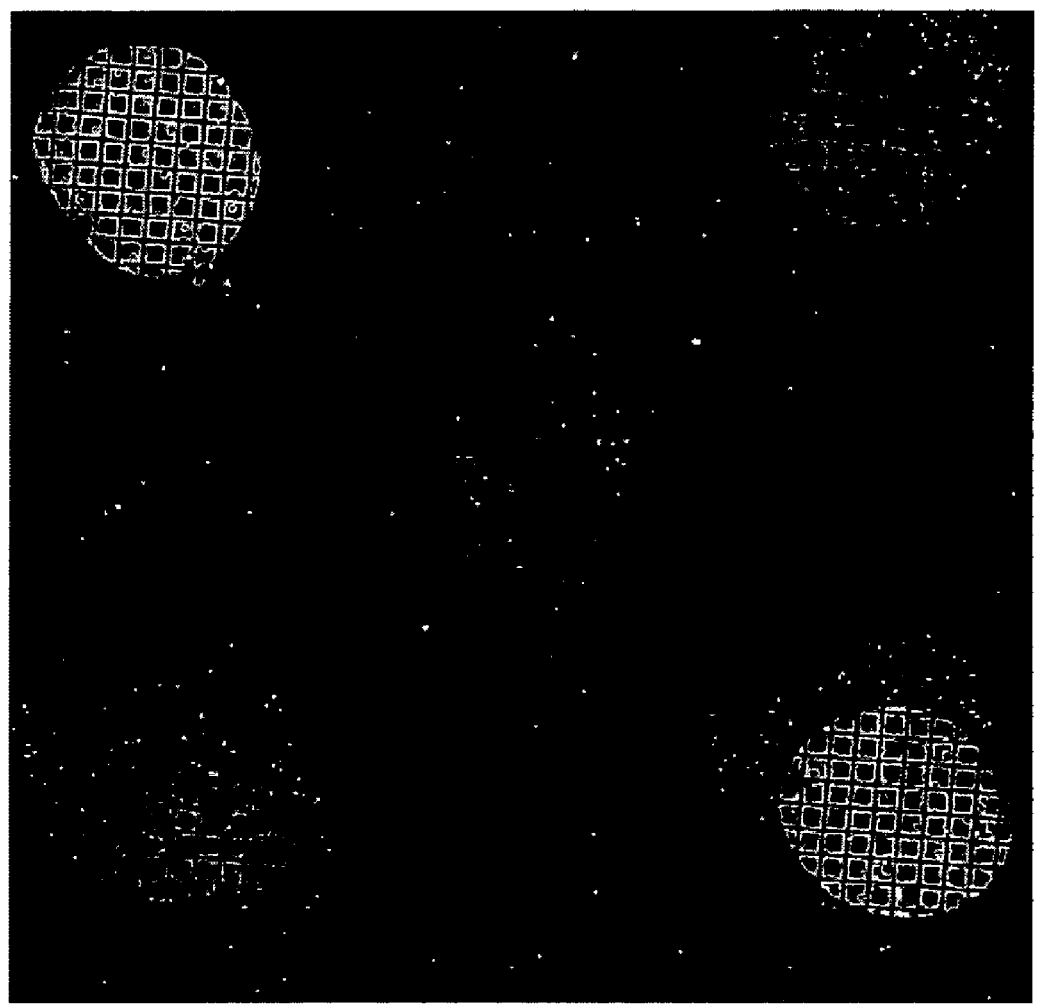

FIG. 15 shows transfers of fluorescence marker to the support member when the sample solution contained anti-Troponin antibodies and the anti-antitrypsin antibody. At top left, Troponin T was bound to the support member; at top right β-galactosidase; at bottom left, Interferonγ; at bottom right α1-antitrypsin. The light-colored areas can be found where the unzip oligo marked the bound anti-Troponin or anti-antitrypsin antibody. Darker areas of non-specific transfer to the support member, where the sensor complex was stamped directly onto receptors not carrying analytes, or onto the passivation (center), can also be seen.

Figure 16:
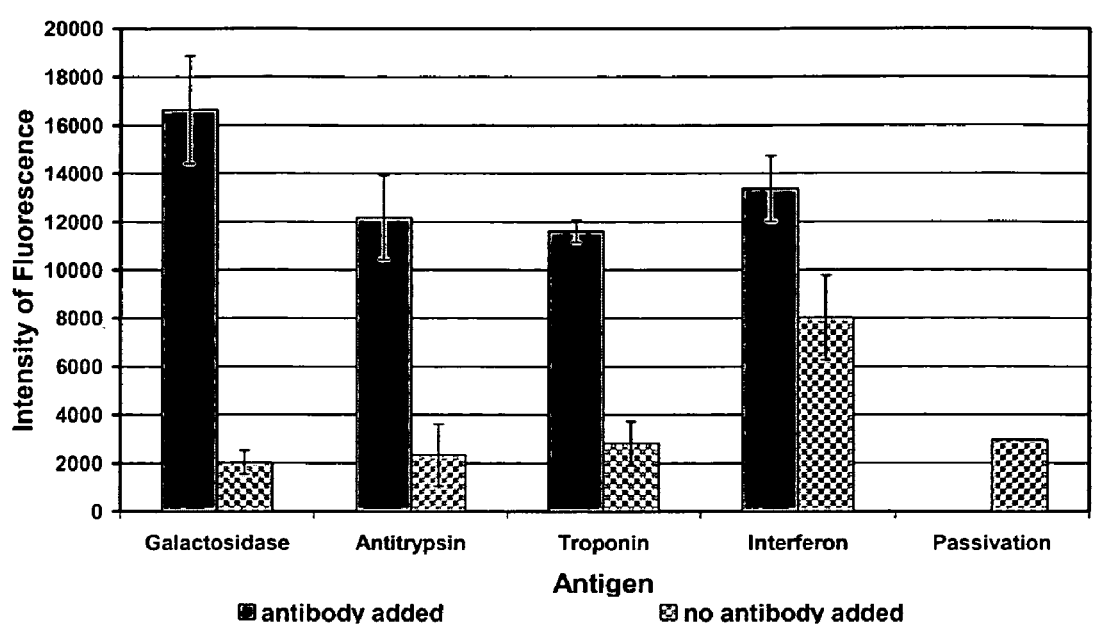

FIG. 16 shows a diagram summarizing the results of experimental Example 6, first arrangement.

Figure 17:
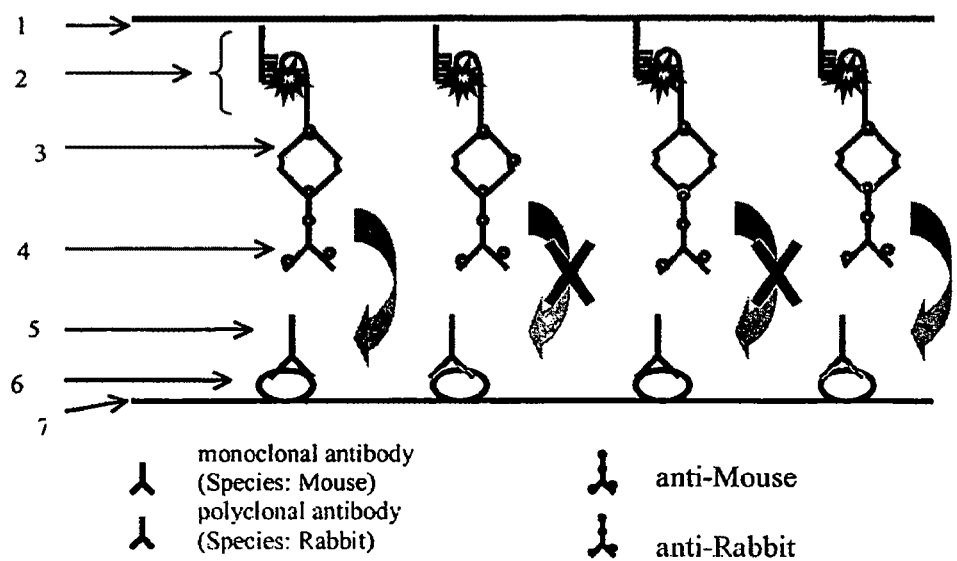

FIG. 17 shows in schematic form the setup of experimental Example 6, second arrangement.

Figure 18:
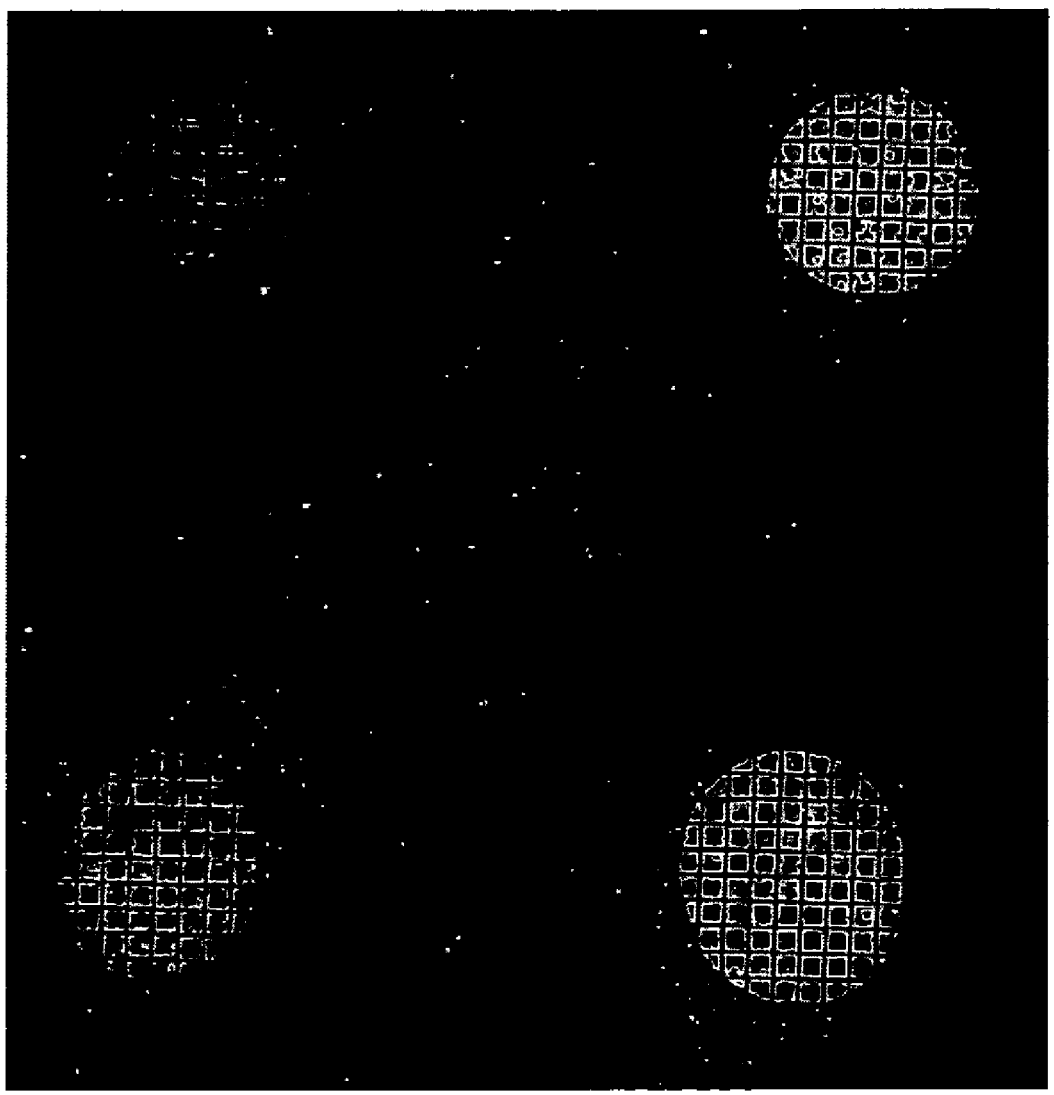

FIG. 18 shows transfers of fluorescence marker to the support member when the sample solution contained the anti-Troponin, anti-β-galactosidase, anti-Interferonγ, and anti-antitrypsin antibodies (monoclonal antibodies, species mouse) and anti-aflatoxin antibody (polyclonal antibody, species rabbit). At top left, Troponin T was bound to the support member; at top right, β-galactosidase; at bottom left, Interferonγ; bottom right, α1-antitrypsin; in the middle, aflatoxin B1-BSA conjugate. The light-colored areas can be found where the unzip oligo marked the bound monoclonal antibodies (species mouse) with the anti-mouse antibody as probe. One can also see the darker areas of non-specific transfer to the support member, where the sensor complex was stamped directly onto the polyclonal antibodies (rabbit species).

Figure 19:
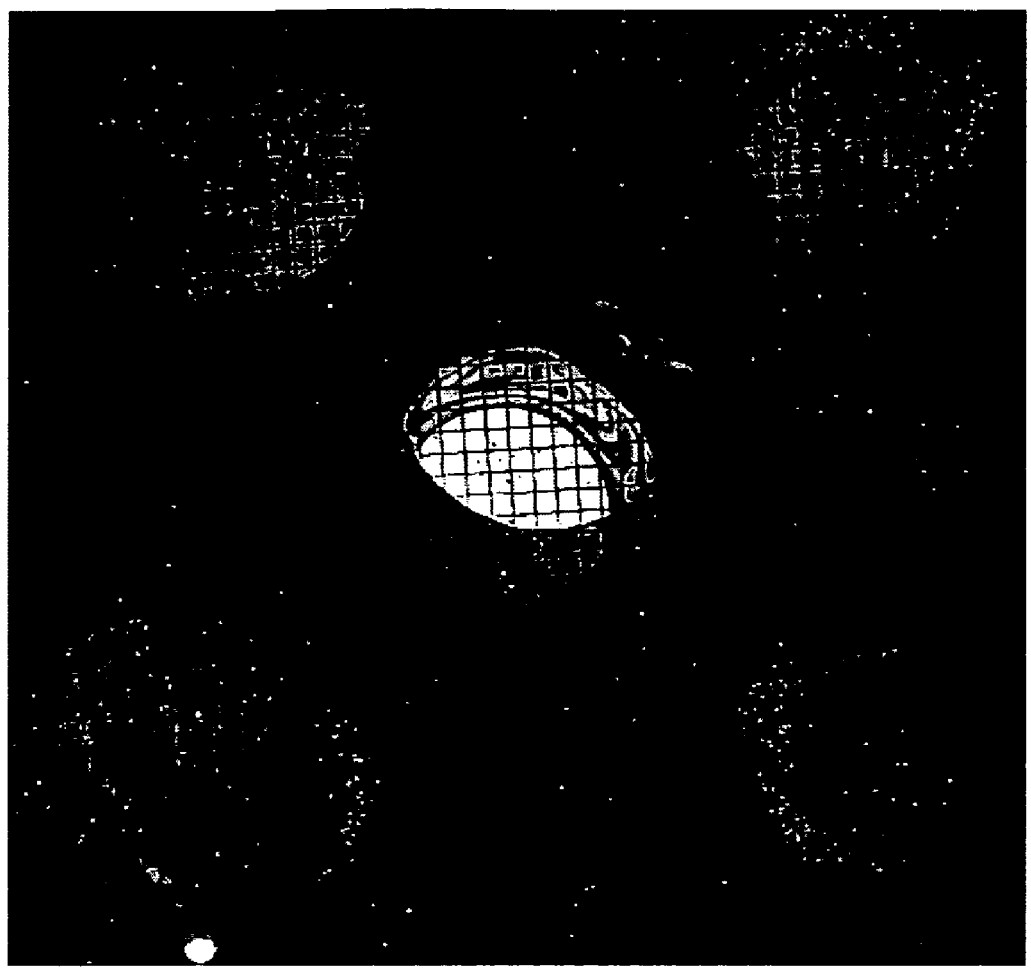

FIG. 19 shows transfers of fluorescence marker to the support member when the sample solution contained the anti-Troponin, anti-β-galactosidase, anti-Interferonγ, and anti-antitrypsin antibodies (monoclonal antibodies, species mouse) and anti-aflatoxin antibody (polyclonal antibody, species rabbit). At top left, Troponin T was bound to the support member; at top right, β-galactosidase; at bottom left, Interferonγ; bottom right, α1-antitrypsin; in the middle, aflatoxin B1-BSA conjugate. The lighter-colored area can be found where the unzip oligo marked the bound anti-aflatoxin antibody with the anti-rabbit-antibody as probe. Darker areas of non-specific transfer to the support member, where the sensor complex was stamped directly onto the antibodies of the species mouse, or onto the passivation, can also be seen.

Figure 20:
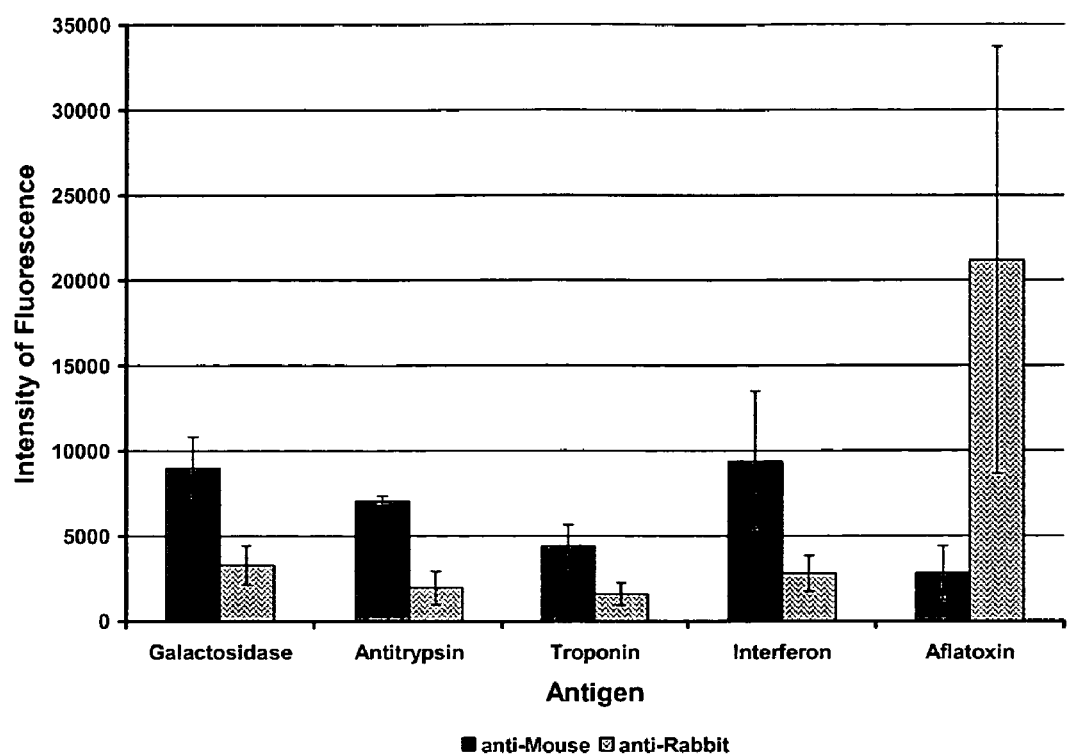

FIG. 20 shows a diagram summarizing the results of experimental Example 6, second arrangement.

Figure 21:
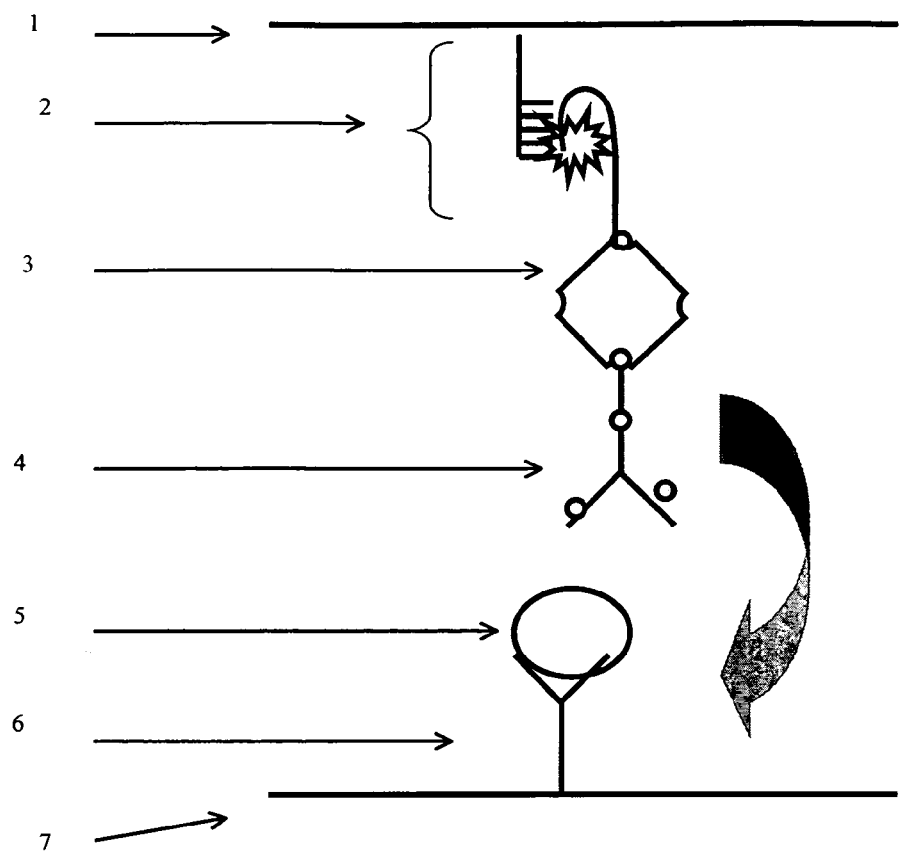

FIG. 21 shows in schematic form the schematic setup of the test described in experimental Example 7.

Figure 22:
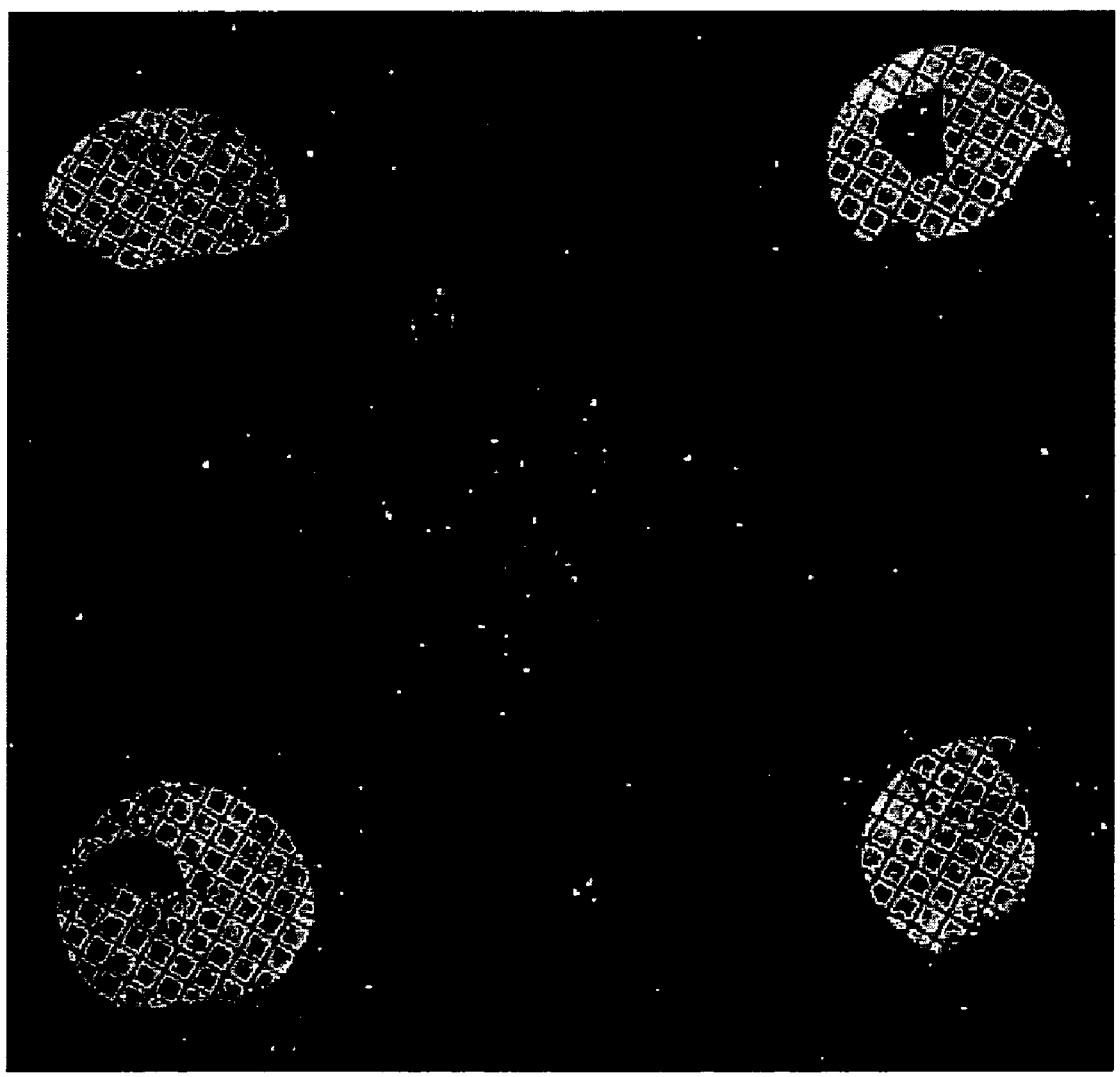

FIG. 22 shows transfers of fluorescence marker onto the support member for the test described in Example 7.

THE TERMS USED TO DESCRIBE THE INVENTION ARE DEFINED AS FOLLOWS

Adsorption: Binding of a ligand or a probe to the chip surface, whereby the binding is not mediated via a receptor.

Receptor: A molecule that binds specifically to a ligand, in particular a molecule that binds specifically to an analyte; In the context of the present invention, any substance or any molecule that has a molecular detection site for an analyte and that can bind the analyte in a specific manner.

Analyte: Refers to all types of molecules, substances or materials to be detected in a sample. Possible analytes are all molecules or complexes, whether organic, inorganic or with organic and inorganic constituents, that have at least two sites capable of binding specifically. In the present description, analytes are also referred to as sample substances or sample molecules.

Ligand: A molecule that binds specifically to a receptor.

Specific: An interaction between two molecules that is based to a high degree on molecular recognition, is said to be specific. Molecular recognition as is typical, for example, of the interaction of an enzyme with a substrate in the substrate binding pocket, of an antibody with an antigen via its "complementarity determining regions" (CDR) or of a single DNA strand with another complementary single strand via Watson-Crick base pairing. A receptor with high specificity binds only one or few ligands within a population of different ligands, whereas a receptor with low specificity binds to several or many ligands within the same population.

Non-specific: An interaction of one molecule with another molecule or body that is not based on a high degree of molecular recognition is said to be non-specific.

Determination: The term is used here for both qualitative and quantitative detection of an analyte, and can include determination of the amount and/or concentration of the analyte. The term also covers the identification and/or any characterization of an analyte on the basis of physical parameters.

Selective probe: A probe that binds only one or very few ligand in a sample mixture.

Direct marking: Marking that is applied directly to an analyte and not by means of a probe.

Indirect marking: Marking that is applied to an analyte by means of a probe.

Cross-reaction: Unwanted, specific interaction of a probe or a receptor with an analyte, or a probe with a receptor.

Probe: A molecule that binds a ligand representing an analyte, and which is used to mark said ligand; in the context of the present invention, any substance or any molecule that has a molecular detection site for an analyte and that can bind the analyte in a specific manner, and that can attach a marker to the analyte. A marker can be bound directly to the probe molecule, or the probe molecule can be joined to a further molecule, in particular to a sensor complex moiety, to which, in turn, a marker is bound.

Binding distance: The distance across which the binding energy must be applied when the complex is dissociated.

Support member: The surface on which the receptors are bound; (conceivable, inter alia, in the form of a plane surface, a film or also, for example, in the form of a cylinder)

Stamp: The surface on which the probes are bound; (conceivable, inter alia, in the form of a plane surface, a film or also, for example, in the form of a cylinder)

Sensor complex: A combination of at least two molecules that can bind specifically to each other and can be separated by applying a tensile force, said tensile force being selected so that the tensile force necessary to separate the molecules is smaller than the tensile force necessary to separate the specifically bound analytes from their binding partners or for separating the immobilized, e.g. covalently bound receptors.

Sample, sample composition: The composition of substances that may possibly contain the analyte(s) to be determined.

Implementation Methods:

Transfer of the Probes:

The probe can be transferred, as described, in such a way that two appropriately configured surfaces are brought into close contact with each other during the stamping procedure.

Said stamping procedure can be performed with a simple apparatus as shown in FIG. 5, for example. The apparatus shown here comprises a base plate (1), two guide rods (2), a carriage (3), stamp member head padding (4), the stamp member head (5) and stamp member padding (6) (see FIG. 5). The base plate, the guide rods and the carriage can be made of metal. The stamp member head padding can consist of foam rubber, and the stamp member head of Plexiglas. The surfaces attached on top (stamp member or support member) can be square in shape and in this embodiment have an area of one $cm^2$ and a thickness of 1 mm. The stamp member padding has the same dimensions, but is smooth on both sides and consists, for example, of very soft PDMS.

The stamp member head padding has the function of bringing the stamp member head into a precisely parallel position in relation to the support member when touching down on the latter. The stamp member padding serves to compensate for slight unevenness between the stamp member and the support member.

In order to perform stamping, the support member is placed on the base plate and the stamp member is placed on the stamp member padding. (Alternatively, the stamp member can also be placed on the base plate and the support member on the stamp member padding, cf. Examples 3 or 4) Both are covered with buffers. The carriage is inserted onto the guide rods and manually lowered until the stamp member comes into contact with the support member. The stamp member and support are also separated manually.

EXAMPLE 1

Sample Complex: Biotin-Streptavidin, Sensor Complex: Iminobiotin-Streptavidin

In order to demonstrate the application of the fluorescence-marked probe, the sample molecules were bound covalently via polymer spacers to the support member. Biotin was used as the analyte, and fluorescence-marked Streptavidin as the probe. Analyte binding to the support member via receptors was replaced here by a covalent binding. The sensor complex is shown as a Streptavidin-iminobiotin binding. Iminobiotin is coupled to the stamp member in a mirror image of the biotin spots on the support member in such a way that, when the surfaces are in contact, the iminobiotin-Streptavidin spots on the stamp member come to lie on the biotin spots.

Since the Streptavidin-iminobiotin binding is weaker than the Streptavidin-biotin binding and the latter is weaker than the covalent binding of the biotin to the support member, the biotin bound to the support member can be detected by targeted transfer of the Streptavidin from the iminobiotin spots to the analytes.

Stamp Construction:

A microstructured stamp member made of PDMS (polydimethyl siloxane) was fabricated. The structures consisted of stamp member feet measuring approx. 100×100 µm, separated by wells approx. 25 µm wide and 1 µm deep. To this end, a mixture comprising a 1:10 mixture of wetting reagent and silicone elastomer (Sylgard 184, Dow Corning) was poured onto an appropriately structured silicon wafer after repeated degassing and incubated for 24 h at room temperature. After polymerization, the structured surface of the stamp member was exposed to an $H_2O$ plasma at 1 mbar in a plasma oven for 60 s.

Coating the Stamp Member:

The oxidized stamp member surface was incubated with 2% triethoxyaldehydsilane (Amchro, Hattersheim, Germany) in 10% $H_2O$ and 88% ethanol for 30 min. The silanized surface was rinsed with ethanol and with ultrapure water, then dried in a stream of nitrogen gas. A bifunctional PEG, one end of which had an amino group and the other end a carboxy group, was linked to the aidehyde groups of the silane. 20 µl of a solution with 20 mg/ml NHS-PEG-COOH (Shearwater, Huntsville, USA) were incubated under a cover glass for 1 h on a stamp member with a surface of 1 $cm^2$. It was rinsed with ultrapure water and dried in a stream of nitrogen gas. The Schiff's bases were then reduced for 30 minutes with 1% by weight sodium borhydride in $H_2O$.

Iminobiotin hydrazide (Sigma, St. Louis) was bound to the carboxy groups of the PEG from a PBS solution (Phosphate Buffered Saline; Sigma) with 5 mg/ml EDC (1-ethyl-3-(3-dimethylamino-propyl)carbiimide; Sigma) and 5 mg/ml NHS (N-hydroxy-succinimide; Sigma, St. Louis). The support member was rinsed with ultrapure water and dried in a stream of nitrogen gas.

The stamp member with the immobilized iminobiotin was incubated with 0.1 mg/ml Alexa-Fluor®-546-Streptavidin conjugate in PBS with 0.02% Vol Tween20, rinsed with rinsed with ultrapure water and dried in a stream of nitrogen gas.

Coating the Support Member:

Glass slides coated with aldehyde silane (CSS type, Genpak, Brighton, UK) were used as the support member. A bifunctional PEG, one end of which had an amino group and the other end a carboxy group, was linked to the aldehyde groups of the silane. 150 µl of a solution with 20 mg/ml NH2-PEG-COOH (Shearwater, Huntsville) were incubated under a 24×60 $mm^2$ cover glass at 40° C. for 2 hrs. It was rinsed with ultrapure water and dried in a stream of nitrogen gas. The Schiffs bases were then reduced for 30 minutes with 1% by weight sodium borhydride in $H_2O$.

Biotin hydrazide (Sigma, St. Louis) was bound to the carboxy groups of the PEG from PBS (Phosphate Buffered Saline; Sigma) with 5 mg/ml EDC (1-ethyl-3-(3-dimethylamino-propyl)carbiimide; Sigma) and 5 mg/ml NHS (N-hydroxy-succinimide; Sigma, Taufkirchen, Germany). The support member was rinsed with ultrapure water and dried in a stream of nitrogen gas.

Probe Transfer:

The surfaces were brought closer together under PBS solution in such a way that the Streptavidin bound to the stamp member could interact with the analyte, the covalently bound biotin, bound to the support member. After incubation for 30 minutes, the surfaces were separated from each other.

Scan:

The support member was scanned with a laser scanner (Perkin Elmer GeneTac LS IV) for the transferring probe, the Streptavidin marked with Alexa-Fluor®-546.

EXAMPLE 2

Sample Complex: DNA-DNA: Sensor Complex: DNA-DNA

The aim is to detect different unmarked DNA molecules in a sample mixture. The receptors are DNA molecules that are bound to the support at their 3' ends. These hybridize specifically with an area at the 5' end of the DNA sample molecule. The associated probes are marked DNA molecules that can hybridize with an area at the 3' end of the sample molecule. The first binding partner of the sensor complex is a DNA molecule, the 5' end of which is bound to the stamp member. The second binding partner of the sensor complex is an area at the 5' end of the DNA probe molecule. By means of this arrangement, the tensile force acts on the two 3' ends of the receptor-analyte duplex and on the two 5' ends of the probe-analyte complex when the two surfaces are pulled apart. At the sensor complex, in contrast, the force acts on the 3' end of the second binding partner of the sensor complex and the 5' end of the first binding partner of the sensor complex, thus enabling the sensor complex to be "unzipped".

The probes are located on the stamp member in a mirror image of the receptor slots on the support member, in such a way that, when the surfaces are in contact, the spots with the probes are always positioned opposite the spots with the associated receptors. If an analyte is bound to the receptors, the associated probe can bind in the contact phase to the 3' end of the analyte. Since the sensor complex hybridized in zip-like manner has a lower stability when a tensile force is applied to the entire conjugate, the sensor complex opens when the surfaces are separated, while the fluorescence-marked probe remains bound to the analyte.

Stamp Construction:

A microstructured stamp member made of PDMS (polydimethyl siloxane) was fabricated. The structures consisted of stamp member feet measuring approx. 100×100 μm, separated by wells approx. 25 μm wide and 1 μm deep. To this end, a mixture comprising a 1:10 mixture of wetting reagent and silicone elastomer (Sylgard 184, Dow Corning) was poured onto an appropriately structured silicon wafer after repeated degassing and incubated for 24 h at room temperature. After polymerization, the structured surface of the stamp member was exposed to an $H_2O$ plasma at 1 mbar in a plasma oven for 60 s.

Coating the Stamp Member:

The oxidized stamp member surface was incubated with 3% aminopropyidimethylethoxysilane (ABCR, Karlsruhe, Germany) in 10% $H_2O$ and 87% ethanol for 30 min. The silanized surface was rinsed with ethanol and with ultrapure water, then dried in a stream of nitrogen gas. A bifunctional NHS-PEG-biotin derivative (Shearwater, Huntsville, USA) was linked to the amino groups of the silane. 20 μl of a solution with 20 mg/ml of the PEG were incubated under a cover glass for 1 h on a stamp member with a 1 cm$^2$ surface. It was rinsed with ultrapure water and dried in a stream of nitrogen gas.

Streptavidin (Sigma, Taufkirchen, Germany) 0.1 mg/ml in PBS was bound to the biotin. Binding to the biotin oligo was done from 25 μM in PBS, 20 μl under a cover glass in 30 min. The fluorescence-marked (Cy3) probes were bound from 25 μM in 5×SSC (saline sodium citric buffer) at room temperature in 3 μl droplets per spot.

Coating the Support Member:

Glass slides coated with aldehyde silane (CSS type, Genpak, Brighton, UK) were used as the support member. A bifunctional PEG, one end of which had an amino group and the other end a carboxy group, was linked to the aldehyde groups of the silane. 150 μl of a solution with 20 mg/ml NH2-PEG-COOH (Shearwater, Huntsville) were incubated under a 24×60 mm$^2$ cover glass at 40° C. for 2 hrs. It was rinsed with ultrapure water and dried in a stream of nitrogen gas. The Schiff's bases were then reduced for 30 minutes with 1% by weight sodium borhydride in $H_2O$.

The carboxy groups of the bound PEG were activated in PBS (Phosphate Buffered Saline; Sigma) for 30 min with 5 mg/ml EDC (1-ethyl-3-(3-dimethylamino-propyl)carbiimide; Sigma) and 5 mg/ml NHS (N-hydroxy-succinimide; Sigma, Taufkirchen). The oligo was bound from 25 μM in PBS, 1 μl droplet per spot within 30 min under a saturated water atmosphere at room temperature.

The analytes were hybridized on from 20 μl of a sample mixture in 5×SSC under cover glass at 70° C. During binding, the sample was able to cool down to room temperature within 30 min.

Probe Transfer:

The surfaces were brought closer together in 5×SSC in such a way that the DNA probes bound to the stamp member could hybridize with the an analytes bound to the support member. After incubation for 45 minutes, the surfaces were separated from each other.

Scan:

The support member was scanned with a laser scanner (Perkin Elmer GeneTac LS IV) for the transferring, fluorescence-marked probe.

EXAMPLE 3

Sample Complex: Biotin-Streptavidin: Sensor Complex: DNA-DNA

The aim is to detect biotinylated, unmarked DNA molecules.

The reference complex is realized as follows (cf. FIG. 6): DNA molecules are bound to the support member at their 5' end (3); these hybridize specifically with an area at the 5' end of other DNA molecules (4), the probes. The probes have an area at the 3' end that for its part can hybridize with areas at the 3' end of the sample molecules (5). The probes also carry a fluorescence marker.

The resultant arrangement is one in which the two oligos forming the reference complex (3+4) are unzipped as soon as sufficient force acts upon the 3' ends of the probes (4).

In this implementation, the reference complexes were bound in the form of four identical spots. The receptor was Streptavidin (6) that had been immobilized to the surface via NHS-PEG3400-biotin.

In this particular implementation, the receptor was not bound in the form of spots, but to the whole of one half of the surface; the other half of the surface was blocked with methoxy-PEG2000 to determine the non-specific transfer (cf. FIG. 7).

The entire surface was incubated with Streptavidin, which could only bind on the side on which the biotin was immobilized. In a further incubation of the entire surface with the biotinylated sample molecules (biotinylated oligo), the latter were bound only where Streptavidin had been immobilized in the previous step.

Where the analyte bound to the receptors (Streptavidin), the associated probe can hybridize to the 3' end of the analyte in the contact phase. Since the sensor complex hybridized in a zip-like manner has a lower resistance to force than the hybridization between the probe and analyte, in which the force acts at the 5' ends of the DNA molecule and hence on all base pairs simultaneously, the sensor complex opens when the surfaces are separated, whereas the fluorescence-marked probe remains bound to the analyte.

Support Member Construction:

A microstructured support member made of PDMS (polydimethyl siloxane) was fabricated. The structures consisted of feet measuring approx. 100×100 μm, separated by wells approx. 25 μm wide and 1 μm deep. To this end, a mixture comprising a 1:10 mixture of wetting reagent and silicone elastomer (Sylgard 184, Dow Corning) was poured between an appropriately structured silicon wafer and a smooth Plexiglas plate after repeated degassing and incubated for 24 h at room temperature. After polymerization, the structured surface was exposed to an $H_2O$ plasma at 1 mbar in a plasma oven for 60 s.

Coating the Support Member:

The oxidized surface was incubated with 3% aminopropyldimethylethoxysilane (ABCR, Karlsruhe, Germany) in 10% $H_2O$ and 87% ethanol for 30 min. The silanized surface was rinsed with ethanol and with ultrapure water, then dried in a stream of nitrogen gas. A bifunctional NHS-PEG-biotin derivative (Shearwater, Huntsville) was linked to the amino groups of the silane. 10 μl of a solution with 20 mg/ml of the PEG were incubated under a cover glass for 1 h on the lower half of the support member (with a surface of 1 cm²). It was rinsed with ultrapure water and dried in a stream of nitrogen gas.

The entire surface was subsequently blocked with a 6 mM solution of NHS-PEG2000-methoxy (Rapp Polymere, Tübingen, Germany). This was done by incubating 25 μl of the solution for 1 h under a round cover glass (12 mm in diameter) in water vapor atmosphere at room temperature. The surface was then rinsed briefly with ultrapure water.

Streptavidin (Sigma, Taufkirchen, Germany) was bound to the entire biotin surface from 5 ml of a 1 μg/ml solution in PBS. The biotinylated sample oligo was incubated over the entire surface from 25 μM in PBS, 20 μl under a cover glass at room temperature for 60 min. It was then washed for 2×10 min and 2×1 min with 1×PBS/0.01% Vol Tween 20 and dried in a stream of nitrogen gas.

Coating the Stamp Member:

The stamp members used were Euray slides made by Exiqon (biozyme article no.: 590.202, product no.: 10212-6225-01, Lot: 40900-14).

Reference complex oligo A was bound according to instructions provided by the slide manufacturer from 2 μM in 1× spotting solution, 1 μl droplet per spot within 12 hrs in a saturated saline solution at room temperature.

The fluorescence-marked (Cy3) probes were bound from 25 μM in 5×SSC at room temperature in 1 μl of droplets per spot under water vapor atmosphere. The stamp member was then washed for 2×10 min with 1×SSC/0.05% Vol Tween 20 and 2×1 min with 0.2×SSC/0.05% Vol Tween.

Probe Transfer:

The surfaces were brought closer together in 5×SSC in such a way that the DNA probes bound to the stamp member could hybridize with the sample molecules bound to the support member. After incubation for 15 minutes, the surfaces were separated from each other.

Since biotin and Streptavidin were immobilized on only one half of the support member, as previously described, analyte (i.e. biotinylated oligo) could only be bound on said half as well. No biotinylated oligo could bind on the half block with methoxy-PEG2000.

Accordingly, wherever the sample oligo is bound, the probe oligo is able on stamping to hybridize with the sample oligo on the PDMS support. When the stamp member and support member are subsequently separated, the marked probe remains bound to the sample molecule, because the unbinding force of the binding between sample molecule and probe is greater than the unzip binding of the reference complex.

The close contact with the stamp member of that portion of the support member to which no analyte bound (upper half of the surface, cf. FIG. 7) serves simultaneously as verification that the probe is transferred only when there is specific binding to the immobilized sample molecule, but not when there is contact with the passivated surface that carries no analytes.

The Following Arrangements were Implemented:

TABLE 1

| | Arrangement: | |
| --- | --- | --- |
| | Upper half of the support member (cf. FIG. 7) | Lower half of the support member (cf. FIG. 7) |
| Support | Control: Methoxy-$PEG_{2000}$ + biotinylated sample oligo - then washed | NHS-$PEG_{3400}$-biotin + Streptavidin + biotinylated sample oligo - then washed |
| Stamp | Reference complex oligos | Reference complex oligos |

Scan:

The stamp member and support member were scanned with a laser scanner (GenePix 4000B, Axon Instruments Inc., USA) at 532 nm for the probe fluorescence-marked with Cy3.

Analysis and Conclusions:

Principle:

The transfer specificity of the fluorescence-marked probe is detected when a significantly higher transfer of fluorescence occur on the half of the surface to which to analyte could bind via Streptavidin than on the surface blocked with methoxy-PEG2000 (FIG. 7 and Table 2).

The fluorescence measured on the support member corresponds to the transferred probe. FIG. 7 shows the fluorescence marker transfers to the support member as measured by the scanner.

NIH Image software was used to analyze the scans. This program enables histograms to be created for selected areas. The histograms show the frequencies of the scanned intensities in the selected area. From the histograms, the mean intensity of the areas of contact with the stamp member feet was determined, as well as the mean intensity at those sites where there were wells in the PDMS. These values were subtracted as background fluorescence from the intensities in the areas of contact to obtain the transfer intensity.

Transfer of the Probe Oligo from the Stamp Member to the Support Member:

TABLE 2

| | Transfer to analyte specific (lower half of the surface, cf. FIG. 7) | Transfer to passivation non-specific (upper half of the surface, cf. FIG. 7) | Specific/ non-specific ratio |
| --- | --- | --- | --- |
| PDMS support after stamping | 1314 +/− 453 | 153 +/− 39 | 11.4:1 |

The mean ratio of specific to non-specific transfer is 11.4:1. Thus, a clear distinction can be made between specific and non-specific transfer. The analyte can be identified.

EXAMPLE 4

Sample Complex: Protein-Haptene: Sensor Complex: DNA-DNA (Detection of the Protein)

Binding via the receptor was replaced here by covalent binding to the surface.

Tests were carried out in which fluorescence-marked binding partners were immobilized on a glass slide via a sensor complex, and the complementary binding partners, or binding partners capable of non-specific binding, were immobilized on a second surface.

This example serves to show that, whenever two surfaces are brought into contact to which binding partners capable of specific binding are immobilized, the probe is transferred only when it encounters the specific binding partner, and that no transfer occurs, however, when on the other surface there is a partner that is not able to bind specifically (e.g. a bound sample molecule unwanted at that site, for example a sample molecule that has simply been adsorbed). It is also shown that, when force is exerted on a chain comprising a sample complex and a reference complex, the zipped binding between two DNA chains, used as the reference complex, is unzipped, and not the binding between two specific binding partners or the covalent immobilization binding, which each have a stronger binding force.

Ultrapure water was used in all tests for washing and for preparing the buffer. Oil-free $N_2$ gas was used for drying. All chemicals were of analytical quality.

a) Preparation of the Glass Slides

Glass slides with aldehyde groups on the surface (CSS type, Genpak, Brighton, UK) were used. These slides were coated with 20 mg/ml HCl—$NH_2$-PEG-COOH (Shearwater, Huntsville, USA) in PBS pH 7.4. 150 µl of solution were used for each slide; the slides were incubated overnight in a moist atmosphere at room temperature, during which they were covered with a 24×60 $mm^2$ cover glass. The slides were then rinsed with water and dried with $N_2$.

The Schiffs bases formed were then reduced with 1% by weight $NaBH_4$ in water for 30 minutes at room temperature. It was then washed with water and blow-dried with $N_2$ gas.

In a further step, oligonucleotides were bound to the PEG-coated slides to provide the linkage between the binding partners and the slide. For this purpose, a first reference complex oligo with an amino group at the 5' end—referred to as Oligo 61—was used. A 25 µmolar dilution of Oligo 61 in PBS plus 7.5 mg/ml EDC was used. 0.6 µl of said solution were swabbed and incubated in a moist atmosphere at 40° C. for 2 hrs. It was then washed with water and blow-dried with $N_2$ gas.

The sequences of the oligos used are as follows:

```
Oligo 61
(reference complex-Oligo A): (SEQ ID NO: 4)
5'-NH2-AAA AAA AAA ATC TCC GGC TTT ACG GCG TAT-3'

Oligo 78 (Unzip, without haptenes): (SEQ ID NO: 1)
5'-Cy3-ATA CGC CGT AAA GCC GGA GAC AGA TAA GAC GCT
ACA TGA AAA AAA AA-3'

Oligo 79 (Unzip, with biotin): (SEQ ID NO: 2)
5'-Cy3-ATA CGC CGT AAA GCC GGA GAC AGA TAA GAC GCT
ACA TGA AAA AAA AA-biotin-3'

Oligo 82 (Unzip, with digoxygenin): (SEQ ID NO: 3)
5'-Cy3-ATA CGC CGT AAA GCC GGA GAC AGA TAA GAC GCT
ACA TGA AAA AAA AA-digoxygenin-3'
``` b) Preparation and Construction of the PDMS Stamp Member

A microstructured stamp member made of 1 mm-thick PDMS (polydimethyl siloxane) was fabricated that had an array of 100×100 $µm^2$ quadrants separated by wells 25 µm wide and 1 µm deep.

To make the PDMS support member, a mixture of silicon elastomer (Sylgard 184, Dow Corning) and wetting reagent (10:1) was poured between a structured silicon wafer and a flat PMMA-(polymethylacrylate) plate after intensive degassing. For polymerization, this arrangement was kept upright at room temperature for 24 hours. The polymerized PDMS was cut into stamp members measuring 1 $cm^2$.

The structured PDMS was functionalized in a plasma cleaner for 60 seconds in the presence of ice. The pressure was reduced to about 2 mbar in this step.

The PDMS pieces treated with plasma were then silanized. This was done by mixing 2% aldehyde ethoxysilane, 88% ethanol and 10% water, and 50 µl/$cm^2$ of this mixture were incubated with the PDMS in a moist atmosphere for 30 minutes at room temperature. The pieces were then dried twice with ethanol, washed three times with water, and dried with $N_2$ gas.

The pieces silanized in this way were then coated with PEG. 20 mg/ml HCl—$NH_2$-PEG-COOH (Shearwater, Huntsville, USA) in PBS pH 7.4 were used. This was done by incubating 150-200 µl solution per PDMS piece (1 $cm^2$) overnight in a moist atmosphere at room temperature. The pieces were then washed with water and blow-dried with $N_2$ gas.

The Schiff's bases formed were then reduced with 1% by weight $NaBH_4$ in water for 30 minutes at room temperature. This was followed by rinsing with water and blow-drying with nitrogen gas.

The functional groups were then activated with EDC/NHS. For this purpose, 10 mg/ml EDC and 10 mg/ml NHS in PBS pH 7.4 were made. The PDMS pieces were each incubated with 30 µl for 30 minutes at room temperature under a cover glass 12 mm in diameter. After that, the pieces were again rinsing with water and blow-dried with $N_2$ gas.

The binding partner capable of specific binding were then bound to the surfaces activated in this way. The binding partners used were antibiotin antibody, anti-digoxygenin antibody, antitrypsin-antibody and Streptavidin. Solutions of 5 mg/ml polyclonal antibiotin antibody, 5 mg/ml polyclonal anti-digoxygenin antibody, 50 µg/ml monoclonal anti-antitrypsin antibody and 100 µg/ml Streptavidin in PBS with 40% glycerine were prepared. 4 µl were swabbed onto a PDMS piece in each case and incubated at room temperature in a moist atmosphere for one hour. The pieces were then washed, firstly with PBS with 0.05% Tween 20 and 1% BSA for 1 minute and then for 2 to 3 minutes with PBS with 0.05% Tween 20.

The functional groups on the PDMS that were still free were then blocked with 2% BSA at room temperature for at least 2 hours. The pieces could also be kept in this blocking solution. Before incubation with the sensor complex on the glass slide, the PDMS was washed with PBS for 2 to 3 minutes, then rinsed with water and dried with $N_2$.

In order to perform the transfer of the binding partners bound via the detector binding to the binding partners that were bound to the PDMS, the PDMS was pressed onto the glass slide in 1×SSC for 30 minutes at room temperature. The two surfaces were then carefully separated, rinsed with water and dried with $N_2$.

The fluorophores transferred in this process were measured with a GenePix 4000 B fluorescence microarray scanner (Axon Instruments Inc., USA). Both surfaces were measured with the 532-nm laser (PDMS: PMT 600 V, 100% energy, focus 100; glass slide: PMT 550 V, 33% energy, focus 0). The background fluorescence of the PDMS (before stamping outside the spots) is about 200, and the background fluorescence of the glass slide (outside the bound oligo) is about 100. The intensities of the spots were measured with the software supplied with the instrument by calculating a mean value in a circular area. This measurement neglects the array-like structure in the patches.

As a control, an unzip oligo was bound from the solution onto the blocked patches of antibody. One type of oligo (with biotin, digoxygenin or without haptene) was diluted in each case in PBS with 10% glycerine and 0.05% Tween 20 for some tests (see Table 8). The final concentration of the oligo was 2 µM or 8 µM. 10 µl of this solution were incubated on the four antibody spots for 30 minutes at room temperature under a cover glass 12 mm in diameter. In the case in which the oligo was dissolved in PBS without Tween 20, the glass slide was only rinsed with water and dried. Otherwise, the glass slide was washed for 2 to 3 minutes with PBS with 0.05% Tween 20, then rinsed with water and dried with $N_2$.

Results

A PDMS piece with four spots of different receptors (antibodies or Streptavidin) was pressed onto a glass slide on which unzip oligo was hybridized with biotin at the first reference complex oligo. A PDMS piece was then scanned with the fluorescence scanner to detect transferred oligos. The experiment was repeated several times, and the results summarized in Table 3. The respective glass slides were scanned before and after stamping, and the results were summarized in Table 4. FIG. 9 shows one example of a fluorescence scan of a PDMS portion after the unzip oligo was stamped with biotin. At top left, Streptavidin solution was linked; at top right, anti-digoxygenine; at bottom left, anti-antitrypsin; at bottom right, antibiotin. The light-colored patches are the antibiotin antibodies and Streptavidin marked with unzip oligo. One can also see darker areas of non-specific transfer of anti-digoxygenin and anti-antitrypsin antibodies.

TABLE 3

Intensity of fluorescence on the PDMS after stamping with unzip oligo-biotin

| Spot | Antibiotin antibody | Anti-digoxygenin antibody | Anti-antitrypsin antibody | Streptavidin | Background between the patches |
|---|---|---|---|---|---|
| 1 | 34918 | 2072 | 1912 | 28084 | 324 |
| 2 | 10294 | 427 | 369 | 6291 | 104 |
| 3 | 39841 | 1831 | 1278 | 24327 | 254 |
| 4 | 38897 | 1738 | 1296 | 24439 | 252 |
| Mean value | 30988 | 1517 | 1214 | 20785 | 238 |
| Standard dev. | 13960 | 740 | 636 | 9819 | 99 |

TABLE 4

Intensity of fluorescence on the glass slide before and after stamping with unzip oligo-digoxygenin

| Stamped | Antibiotin antibody | | Anti-digoxygenin antibody | | Anti-antitrypsin antibody | | Streptavidin | | Background between the patches | |
|---|---|---|---|---|---|---|---|---|---|---|
| | before | after | before | after | before | after | before | after | before | after |
| 1 | 20723 | 8131 | 19015 | 8103 | 24581 | 10771 | 23498 | 9306 | 4337 | 2194 |
| 2 | 30712 | 22592 | 34469 | 26696 | 40265 | 29454 | 38061 | 27448 | 8138 | 6628 |
| 3 | 45484 | 28470 | 46352 | 33597 | 45343 | 30158 | 47983 | 30202 | 10648 | 8232 |
| 4 | 25108 | 21975 | 26660 | 21127 | 32111 | 28045 | 32506 | 23107 | 4856 | 5242 |
| Mean value | 30507 | 20292 | 31624 | 22381 | 35575 | 24607 | 35512 | 22516 | 6995 | 5574 |
| Std. dev. | 10789 | 8620 | 11671 | 10799 | 9134 | 9266 | 10253 | 9278 | 2960 | 2563 |

A PDMS piece with four spots of different receptors (antibodies and/or Streptavidin) was pressed onto a glass slide on which unzip oligo with digoxygenin was hybridized at the first reference complex. A PDMS piece was then scanned for transferred oligos with the fluorescence scanner. The experiment was repeated several times, and the results summarized in Table 5. The respective slides were scanned before and after stamping. The results are summarized in Table 6. An example of a fluorescence scan of a PDMS stamped with an unzip oligo with digoxygenin is shown in FIG. 10. At top left, Streptavidin solution was linked; at top right, anti-digoxygenine; at bottom left, anti-antitrypsin; at bottom right, antibiotin. The only light-colored area is where anti-digoxygenin antibody was immobilized; all other spots are very weak.

TABLE 5

Intensity of fluorescence on the PDMS after stamping with unzip oligo-digoxygenin

| Spot | Antibiotin antibody | Anti-digoxygenin antibody | Anti-antitrypsin antibody | Streptavidin | Background between the spots |
|---|---|---|---|---|---|
| 1 | 2031 | 16810 | 1770 | 1900 | 752 |
| 2 | 1107 | 25362 | 1284 | 1209 | 349 |
| 3 | 1091 | 25047 | 1282 | 1213 | 351 |
| Mean value | 1410 | 22406 | 1445 | 1441 | 484 |
| Standard dev. | 538 | 4849 | 281 | 398 | 232 |

TABLE 6

Intensity of fluorescence on the glass slide before and after stamping with unzip oligo-digoxygenin

| Stamped | Antibiotin antibody | | Anti-digoxygenin antibody | | Anti-antitrypsin antibody | | Streptavidin | | Background between the spots | |
|---|---|---|---|---|---|---|---|---|---|---|
| | before | after | before | after | before | after | before | after | before | after |
| 1 | 30857 | 17340 | 29939 | 15270 | 34023 | 17562 | 32886 | 16116 | 15167 | 8802 |
| 2 | 54238 | 28446 | 51522 | 34243 | 53214 | 34678 | 51641 | 37493 | 19637 | 13269 |
| 3 | 42921 | 47280 | 42044 | 41268 | 44449 | 46901 | 47121 | 41584 | 20181 | 25678 |
| Mean value | 42672 | 31022 | 41168 | 30260 | 43895 | 33047 | 43883 | 31731 | 18328 | 15916 |
| Std. dev. | 11692 | 15135 | 10818 | 13449 | 9607 | 14737 | 9788 | 13677 | 2751 | 8744 |

A PDMS piece with four spots of different receptors (antibodies and/or Streptavidin) was pressed onto a glass slide on which unzip oligo without haptene was hybridized at the first reference complex. A PDMS piece was then scanned for transferred oligos with the fluorescence scanner. The result is summarized in Table 7. The respective glass slides were scanned before and after stamping, and the result summarized in Table 8.

TABLE 7

Intensity of fluorescence on the PDMS after stamping unzip oligo without haptene

| Spot | Antibiotin antibody | Anti-digoxygenin antibody | Anti-antitrypsin antibody | Streptavidin | Background between the spots |
|---|---|---|---|---|---|
| | 1876 | 1685 | 1934 | 1823 | 429 |

TABLE 8

Intensity of fluorescence on the glass slide before and after stamping with unzip oligo without haptene

| Stamped | Antibiotin antibody | | Anti-digoxygenin antibody | | Anti-antitrypsin antibody | | Streptavidin | | Background between the spots | |
|---|---|---|---|---|---|---|---|---|---|---|
| | before | after | before | after | before | after | before | after | before | after |
| | 54316 | 39966 | 61090 | 40687 | 50410 | 39049 | 61371 | 44179 | 8604 | 8048 |

As a control, the oligos with and without haptenes were also bound from the solution onto protein spots. The resulting intensities of fluorescence are summarized in Table 9.

TABLE 9

Intensity of fluorescence on the spots after binding oligos from the solution (Oligo 78 = unzip oligo without haptene, Oligo 79 = unzip oligo with biotin, Oligo 82 = unzip oligo with digoxygenin, PBST = PBS with 0.05% Tween 20)

| | Binding buffer | Antibiotin antibody | Anti-digoxygenin antibody | Anti-antitrypsin antibody | Streptavidin | Background between the spots |
|---|---|---|---|---|---|---|
| Oligo 79 (2 µM) | PBST | 2560 | 281 | 58 | 7624 | 54 |
| Oligo 79 (8 µM) | PBST | 14569 | 493 | 100 | 1490 | 105 |
| Oligo 79 (8 µM) | PBST | 18441 | 72 | 93 | 4237 | 93 |
| Oligo 79 (8 µM) | PBS | 13330 | 97 | 90 | 3692 | 74 |
| Oligo 82 (2 µM) | PBST | 373 | 10472 | 549 | 659 | 522 |
| Oligo 82 (8 µM) | PBST | 550 | 5468 | 336 | 628 | 494 |
| Oligo 82 (8 µM) | PBST | 234 | 2600 | 167 | 243 | 156 |
| Oligo 82 (8 µM) | PBS | 490 | 3083 | 319 | 313 | 271 |
| Oligo 78 (2 µM) | PBST | 225 | 196 | 135 | 175 | 118 |
| Oligo 78 (8 µM) | PBST | 187 | 434 | 249 | 791 | 251 |

The results obtained from stamping and summarized in FIG. 11 show a highly specific transfer of the unzip oligo onto the corresponding proteins (intensity of fluorescence between 20,000 and 30,000), whereas non-specific transfer onto the other protein spots is rather low (about 1600) and independent of the oligo used. The ratio of specific to non-specific transfer is greater than 10:1.

FIG. 11 shows a summary of the results obtained from stamping the unzip oligo with and without haptene onto four different protein spots. Binding of the oligo from the solution results not only in fewer intensive spots in the case of a specific binding (about 5,800), but also in less non-specific binding (about 300). This leads to a similar ratio of specific to non-specific binding. The higher intensities of the spots reached by stamping are due to a higher local concentration. Neither the presence of Tween 20 in the binding buffer nor different washing steps had a significant influence on antigen binding.

EXAMPLE 5

Sample Complex: Antibody-antigen: Sensor Complex: DNA-DNA (Detection of Antigen)

The aim is to detect different unmarked proteins in a sample mixture. The receptors are biotinylated antibodies that are bound to the support member via Streptavidin. The associated probes are DNA-antibody fragment conjugates that carry a fluorescence marker. The sensor complex is shown as two DNA molecules hybridized in zip-like manner. The first binding partner of the sensor complex is a DNA molecule, the 5' end of which is bound via an amino group to the stamp member. The second binding partner of the sensor complex is shown as a fluorescence-marked DNA molecule that has a thiol group at the 3' end and is also coupled to a free C-terminal cysteine of the antibody fragment.

The probes are located on the stamp member in a mirror image of the receptor slots on the support member, in such a way that, when the surfaces are in contact, the spots with the probes are always positioned opposite the spots with the associated receptors. If an analyte is bound to the receptors, the associated probe can bind to the analyte in the contact phase. Since the sensor complex hybridized in zip-like manner has a lower stability when a tensile force is applied to the entire conjugate than the antibody(fragment)-antigen binding, the sensor complex opens when the surfaces are separated, while the fluorescence-marked probe remains bound to the analyte.

Stamp Construction:

A microstructured stamp member made of PDMS (polydimethyl siloxane) was fabricated. The structures consisted of stamp member feet measuring approx. 100×100 µm, separated by wells approx. 25 µm wide and 1 µm deep. To this end, a mixture comprising a 1:10 mixture of wetting reagent and silicone elastomer (Sylgard 184, Dow Corning) was poured onto an appropriately structured silicon wafer after repeated degassing and incubated for 24 h at room temperature. After polymerization, the structured surface of the stamp member was exposed to an $H_2O$ plasma at 1 mbar in a plasma oven for 60 s.

Coating the Stamp Member:

The oxidized stamp member surface was incubated with 2% aminopropyldimethylethoxysilane (ABCR, Karlsruhe, Germany) in 10% $H_2O$ and 88% ethanol for 30 min. The silanized surface was rinsed with ethanol and with ultrapure water, then dried in a stream of nitrogen gas. A bifunctional PEG, one end of which had an NHS group and the other end a carboxy group, was linked to the aldehyde groups of the silane. 25 µl of a solution with 20 mM NHS-PEG-COOH (Shearwater, Huntsville) were incubated under a cover glass for 2 h on a stamp member with a surface of 1 $cm^2$. It was rinsed with ultrapure water and dried in a stream of nitrogen gas.

The first binding partner of the force sensor was bound via an amino group to the carboxy groups of the PEG from 25 µM solution of the binding partner in PBS (Phosphate Buffered Saline; Sigma) with 5 mg/ml EDC (1-ethyl-3-(3-dimethylamino-propyl)carbiimide; Sigma) and 5 mg/ml NHS (N-hydroxy-succinimide; Sigma, St. Louis) using 20 µl/$cm^2$ under a cover glass for 30 min.

The probe was fabricated by coupling the second binding partner of the force sensor, an oligo fluorescence-marked with Cy3 via a thiol group to the C-terminal cysteine of the antibody fragment.

The probes were hybridized from 3 µl droplets per spot from a 25 µM solution in 5×SSC (saline sodium citric buffer; Sigma, Taufkirchen) at room temperature.

Coating the Support Member:

The surface was treated for two hours with NaOH, 10 g in 40 ml $H_2O$ and 60 ml ethanol. The stamp member surface was incubated with 3% aminopropyldimethylethoxysilane (ABCR, Karlsruhe, Germany) in 10% $H_2O$ and 87% ethanol for 30 min. The silanized surface was rinsed with ethanol and with ultrapure water, then dried in a stream of nitrogen gas. A bifunctional NHS-PEG-biotin derivative (Shearwater, Huntsville) was linked to the amino groups of the silane. 150 µl of a solution with 20 mg/ml of the PEG were incubated under a 24×60 $mm^2$ cover glass for 1 h. It was rinsed with ultrapure water and dried in a stream of nitrogen gas.

Streptavidin (Sigma, Taufkirchen, Germany) was bound to the biotin from 0.1 mg/mi in PBS with 0.05% Vol Tween. This was done by incubated 150 µl of the Streptavidin solution under a 24×60 $mm_2$ cover glass for 30 min. The biotinylated receptor antibodies were bound to the Streptavidin as 1 µl spots from 0.5 mg/ml in PBS with 0.05% Vol Tween and 40% glycerine. The analytes were bound from a sample mixture in PBS with 0.05% Vol Tween.

Probe Transfer:

The surfaces were brought closer together under PBS with 0.05% Tween in such a way that the probes bound on the stamp member could bind with the analytes spotted on the support member. After incubation for 30 minutes, the surfaces were separated from each other.

Scan:

The support member was scanned with a laser scanner for the fluorescence-marked transferring probe.

EXAMPLE 6

Sample Complex: Antibody-antigen: Sensor Complex: DNA-DNA (Detection of the Antibody)

The aim is to detect different unmarked antibodies from a mixture of antibodies. The receptors are represented by the respective antigen that the antibody is supposed to recognize. The antigens are bound covalently to the support member. The associated probes are complexes comprised of DNA and secondary, species-specific antibodies that specifically recognize the respective sample antibodies. The binding between secondary antibodies and DNA is realized with biotinylated DNA and biotinylated antibodies that are bound via Streptavidin. The sensor complex is shown as two DNA molecules hybridized in zip-like manner. The first binding partner of the sensor complex is a DNA molecule, the 5' end of which is bound via an amino group to the stamp member. The second binding partner of the sensor complex is a fluorescence-marked DNA molecule with biotin at its 3' end. This biotin enables linkage with Streptavidin and hence the binding with the secondary antibody (cf. FIG. 12).

The probes are located on the stamp member in a mirror image of the receptor slots on the support member, in such a way that, when the surfaces are in contact, the spots with the probes are always positioned opposite the spots with the associated receptors. If an analyte is bound to the receptors, the associated probe can bind to the analyte in the contact phase. Since the sensor complex hybridized in zip-like manner has a lower stability when a tensile force is applied to the entire conjugate than the other bindings in the conjugate (Streptavidin-biotin bindings, antigen-antibody interaction as well as the covalent binding of the antigen to the support member), the sensor complex opens when the surfaces are separated and the fluorescence-marked probe remains bound to the analyte.

Stamp Construction:

A microstructured stamp member made of PDMS (polydimethyl siloxane) was fabricated. The structures consisted of stamp member feet measuring approx. 100×100 µm, separated by wells approx. 25 µm wide and 1 µm. To this end, a mixture comprising a 1:10 mixture of wetting reagent and silicone elastomer (Sylgard 184, Dow Corning) was poured onto an appropriately structured silicon wafer after repeated degassing and incubated for 24 h at room temperature. After polymerization, the structured surface of the stamp member was exposed to an $H_2O$ plasma at 2 mbar in a plasma oven for 60 s.

Coating the Stamp Member:

The oxidized surface was incubated with a solution comprising 2% aminopropyldimethylethoxysilane (ABCR, Karlsruhe, Germany) in 10% $H_2O$ and 88% ethanol for 30 min. The silanized surface was rinsed with ethanol and ultrapure water, then dried in a stream of nitrogen gas. A bifunctional PEG derivative, one end of which had an amino-reactive NHS group (N-hydroxy-succinimide) and the other end a carboxy group, was linked to the amino groups of the silane. 25 µl of a 20 mM NHS-PEG-COOH solution (Shearwater, Huntsville, USA) (in $H_2O$) were incubated under a round cover glass 12 mm in diameter for 2 h in a moist atmosphere at room temperature. It was rinsed with ultrapure water and dried in a stream of nitrogen gas. Surface amino groups that had not yet reacted were blocked using with a 6 mM solution (in $H_2O$) of NHS-PEG-methoxy (Rapp Polymere, Tübingen, Germany). This was done by incubating 25 µl of the solution for 1 h under a round cover glass.

Once the latter step has been carried out, a surface with carboxy groups for coupling with the first reference complex oligo is available. This was done by mixing the first reference complex oligo (sequence: see Annex, cf. Example 4) with an aqueous EDC solution (1-ethyl-3-(3-dimethylamino-propyl)carbiimide; Sigma, Taufkirchen, Germany). The final concentration of oligo was 25 µM, and the EDC concentration was 50 mM. The freshly mixed solution was spotted (in 5×1 µl spots) onto the surface and incubated for 2 h at room temperature. The surface was then rinsed with 1×SSC+0.5% SDS for 2×30 min and blocked overnight with 1% by weight bovine serum albumin (BSA) at 4° C. To finish, the surface was rinsed with water and dried in a stream of nitrogen gas.

Structure of Probe:

In order to hybridize the unzip oligo with biotin (sequence: see Annex, cf. Example 4), a 2 µM solution in 5×SSC was made. 10 µl of this hybridization solution were incubated under a round cover glass (12 mm in diameter) for 1 h at room temperature in a moist atmosphere. It was washed for 3×5 min with 1×SSC+0.1% SDS, rinsed with ultrapure water and dried in a stream of nitrogen gas.

Binding the Streptavidin (Sigma, Taufkirchen, Germany) was done by agitating the PDMS pieces in a bowl filled with a Streptavidin solution. The concentration of Streptavidin was 1 µg/ml in PBS+0.2% BSA. The PDMS pieces were agitated in 5 ml solution for 45 min at room temperature and subsequently washed with PBS+0.05% Tween 20.

Similarly, the biotinylated secondary anti-mouse antibody (Molecular Probes, Leiden, Netherlands) from a large volume of solution (5 ml) was bound to the Streptavidin. The master antibody solution was similarly diluted to 1 µg/ml in PBS+0.2% BSA. The PDMS pieces were agitated in this solution for 1 h, washed with PBS+0.05% Tween, rinsed with water and dried in a stream of nitrogen gas.

In those experimental arrangements in which the probe is created with the anti-rabbit antibody (Molecular Probes, Leiden, Netherlands), the latter was used in the same way as described for the anti-mouse antibody.

Coating the Support Member:

Glass slides coated with aldehyde silane (CSS type, Genpak, Brighton, UK) were used as the support member. A bifunctional PEG, one end of which had an amino group and the other end a carboxy group, was linked to the aldehyde groups of the silane. 200 µl of a 6 mM NHS-PEG-COOH solution (Shearwater, Huntsville, USA) (in $H_2O$) were incubated under a round, 24×60 $mm^2$ cover glass for 2 h in a moist atmosphere at room temperature. It was rinsed with ultrapure water and dried in a stream of nitrogen gas. The Schiff's bases were then reduced for 30 minutes with 1% by weight sodium borhydride in $H_2O$.

Once the latter step has been carried out, a surface with carboxy groups for coupling the antigens is available. This was done by activating the carboxy groups with EDC and NHS (N-hydroxy-succinimide; Sigma, Taufkirchen, Germany) over the whole surface. The surface was incubated with a freshly prepared solution (200 µl) of 50 mM EDC and 50 mM NHS under a 24×60 $mm^2$ cover glass for 30 min in a moist atmosphere at room temperature. It was then rinsed with water and dried in a stream of nitrogen gas.

Immobilization of the Antigens:

Starting with their parent solution, all antigens were diluted in 2% vol glycerine (final concentration: 20 µg/ml-100 µg/ml). The concentrations used were determined in tests in which the antigens were immobilized on the support member and subsequently detected via their monoclonal and fluorescence-marked secondary antibodies. The concentration measured for intensive and homogenous spots was then used for the further tests. The antigens used and their optimal concentrations are summarized in the following Table:

| Antigen | Molecular weight | Concentration | Producer |
|---|---|---|---|
| β-galactosidase | 450 kDa | 50 µg/ml | Roche, Mannheim |
| α₁anti-antitrypsin | 52 kDa | 100 µg/ml | Calbiochem, Darmstadt |
| Interferon γ | 16.7 kDa | 20 µg/ml | Biotrend, Cologne |
| Troponin T | not known | 25 µg/ml | Biotrend, Cologne |

The spot solutions of the various antigens were manually pipetted as 1 µl spots onto the support material. The combination and arrangement of the various antigens varied according to the particular experimental arrangement. The spots were incubated on the surface for 1 h at room temperature and washed off with PBS. The activated carboxy groups remaining in addition to the spots were blocked overnight with 1% by weight BSA in PBS. To finish, the surface was washed with PBS+0.05% Tween 20.

For a negative control, an antigen was required that is recognized by a polyclonal antibody, e.g. from rabbit. A BSA conjugate of aflatoxin B1 was used for this purpose (Sigma, Taufkirchen, Germany). The conjugate was spotted in a concentration of 10 µg/ml in accordance with the rule specified above.

Binding of Analytes (Monoclonal Antibodies) from a Mixture:

The monoclonal antibodies against the above antigens are summarizes in the following Table:

| Antibody against | Species | Concentration | Producer |
|---|---|---|---|
| β-galactosidase | Mouse monoclonal | 0.5 µg/ml | Roche, Mannheim |
| α₁anti-antitrypsin | Mouse monoclonal | 0.5 µg/ml | Calbiochem, Darmstadt |
| Interferon γ | Mouse monoclonal | 0.5 µg/ml | Biotrend, Cologne |
| Troponin T | Mouse monoclonal | 0.5 µg/ml | Biotrend, Cologne |

The antibodies were diluted in PBS+0.2% BSA to the specified concentration. Incubation was carried out in 4 ml solution on an agitator for 1 h at room temperature. The particular antibodies added to the incubation solution depended on the respective experimental arrangement. After incubation, the slides were washed in PBS+0.05% Tween, rinsed with water and dried in a stream of nitrogen gas.

As a negative control, a polyclonal antibody from rabbit was bound to the aflatoxin B1 BSA conjugate. This, too, was added to the sample solution depending on the specific experimental arrangement. The polyclonal antibodies were diluted 1:8000 in PBS+0.2% BSA. In the stamping step, this rabbit antibody may only be marked by a probe with an anti-rabbit antibody, and not by the anti-mouse antibody used to detect the monoclonal antibodies.

Stamping:

The surfaces were brought closer together under PBS that the probes spotted on the stamp member could come into contact and interact with the analytes on the support member. After incubation for 30 minutes, the surfaces were separated from each other.

Scan:

The support member was scanned with a laser scanner for the fluorescence-marked transferring probe.

Analysis and Conclusions:

The transfer specificity of the fluorescence-marked probe was sensed with two different setups. The aim in the first experimental arrangement was to detect that a significantly higher fluorescence yield occurred when the analyte bound to its antigen than when there was direct contact between the receptor and the probe (cf. FIG. 13). The second arrangement shows that bound analytes are marked by the probe only when the probe is specific to the respective analyte (cf. FIG. 17).

1st Arrangement: Transfer of the Probe Only when Analytes are Bound

This experimental setup was so arranged that transfers can be compared when, on the one hand, the analyte bound from solution to the receptor, and, on the other hand, no analyte bound to the receptor, so that direct contact between the probe and receptor can take place.

For this purpose, the probe was constructed from unzip complex, Streptavidin and the secondary antibody (anti-mouse). Four spots were placed in such a way that each met up with one of the four antigen spots on the support member. Another spot was disposed so that it would not coincide with a spot on the support member during stamping. This latter spot acted as a control for non-specific transfer to the passivation. The four different antigens were spotted onto the support member in each of two specified areas. This was done in each case by pipetting 1 µl of each antigen onto the support member. The spots were arranged on the two surfaces according to the following scheme:

| Support material: | | Stamp: | |
|---|---|---|---|
| Troponin T | β-galactosidase | Anti-mouse | Anti-mouse |
| | | Anti-mouse | |
| Interferon γ | α1-Antitrypsin | Anti-mouse | Anti-mouse |

A specific transfer of the fluorescence marker of the force sensor during stamping is detected when the receptor spots (antigen) whose monoclonal antibodies were added to the sample solution exhibit a significantly higher fluorescence than the antigen spots whose antibody were not present in this arrangement. Two experimental arrangements were conducted, whereby the sample solution in one arrangement contained the anti-β-galactosidase and the anti-interferon γ antibody, and in the other arrangement the antibodies against Troponin T and α1-antitrypsin. All arrangements were repeated several times, and mean values were determined.

FIG. 14 shows the transfers of fluorescence marker onto the support member as measured by the scanner when the sample solution contained the anti-β-galactosidase and the anti-Interferon γ antibody. FIG. 15 shows the arrangement with the antibodies against Troponin T and α1-antitrypsin.

NIH Image software was used to analyze the scans. This program enables histograms to be created for selected areas. The histograms show the frequencies of the scanned intensities in the selected area. From the histograms, the mean intensity of the contact surfaces with the stamp member feet was determined, as well as the mean intensity at those sites where there were wells in the PDMS. These values were subtracted as background fluorescence from the intensities in the areas of contact to obtain the transfer intensity. The mean values and standard deviations of the measurements are summarized in the following table and in FIG. 16:

| | Intensities of fluorescence transfers on addition of anti- | |
|---|---|---|
| Antigen | β-galactosidase & Interferon γ | α1-antitrypsin & Troponin T |
| β-galactosidase | 16643 ± 2227 | 2018 ± 488 |
| α1-antitrypsin | 2335 ± 1285 | 12176 ± 1744 |
| Interferon γ | 13366 ± 1362 | 8022 ± 1751 |
| Troponin T | 2820 ± 907 | 11613 ± 457 |
| Passivation | 2681 ± 1247 | 3216 ± 224 |

The comparison of transfers to an antigen when antibody was bound or when there was direct contact between receptor and probe shows, for β-galactosidase, α1-antitrypsin and Troponin T, that the transfer with antibody is significantly higher than the transfer to the passivation or directly to the antigen. The ratio of specific to non-specific transfer therefore permits the conclusion that the transfer of fluorescence marker to the antibody is a case of specific transfer. The non-specific transfer for these proteins is in the same order of magnitude as the transfer to the passivation.

For Interferon γ, the difference between specific and non-specific transfer is substantially smaller. The proportion of specific transfer is nevertheless greater.

2nd Arrangement: Transfer of Probe Only on Specific Interaction Between Analyte and Probe This test arrangement was structured in such a way that a comparison can be made between the transfer when the probe is specific for the analyte, on the one hand, and when the analyte is brought into contact with a non-specific probe, on the other hand.

To this end, the probe on the stamp member was constructed either from unzip complex, Streptavidin and secondary anti-mouse antibody, or from unzip complex, Streptavidin and secondary anti-rabbit antibody. Five spots were placed in such a way that each coincided with one of the five antigen spots on the support member. The five different antigens were spotted onto the support member in each of two defined areas. This was done in each case by pipetting 1 µl of each antigen onto the support member. The spots were arranged on the two surfaces according to the following scheme:

| Support material: | | Stamp: | |
|---|---|---|---|
| Troponin T | β-galactosidase | sec. antibody | sec. antibody |
| AflatoxinB1-BSA | | sec. antibody | |
| Interferon γ | α1-Antitrypsin | sec. antibody | sec. antibody |

A specific transfer of the fluorescence marker is detected when, after stamping, the antigen spots that bound to their monoclonal (murine) antibodies exhibit a significantly higher fluorescence when the probe contains the anti-mouse antibody than the aflatoxinB1-BSA that binds a polyclonal antibody from rabbit. On the other hand, the spot from aflatoxinB1-BSA must exhibit a higher intensity than the other antigen spots when the probe contains the anti-rabbit antibody.

Two experimental arrangements were conducted, whereby the probe in one arrangement contained the anti-mouse antibody and in the other arrangement the anti-rabbit antibody. All arrangements were repeated several times, and mean values from three measurements were determined.

FIG. 18 shows the transfers of fluorescence marker onto the support member as measured by the scanner when the anti-mouse antibody was used for the probe. FIG. 19 shows the arrangement with the anti-rabbit antibody.

The scans were analyzed in the same way as described for arrangement 1. The mean values and standard deviations of the measurements are summarized in the following table and in FIG. 20:

|  | Intensities of fluorescence transfers for a probe with anti- | |
| --- | --- | --- |
| Antigen | Mouse | Rabbit |
| β-galactosidase | 8955 ± 1861 | 3279 ± 1138 |
| α$_1$-antitrypsin | 7035 ± 300 | 1947 ± 977 |
| Interferon γ | 9358 ± 4131 | 2788 ± 1053 |
| Troponin T | 4394 ± 1250 | 1582 ± 659 |
| AflatoxinB1-BSA | 2822 ± 1577 | 21168 ± 12524 |

The comparison of transfers with the anti-mouse antibody and the anti-rabbit antibody shows clearly that β-galactosidase, α1-antitrypsin, Troponin T and Interferon γ from anti-mouse antibody are fluorescence-marked to a significantly stronger degree than those from anti-rabbit antibody. Since these proteins bind the monoclonal (murine) antibodies from the sample solution, transfer is about three times greater with the anti-mouse antibody in the case of specific interaction. In this arrangement, the non-specific transfer is that to the aflatoxinB1-BSA spot (cf. FIG. 18). On the other hand, a significantly higher transfer to the aflatoxinB1-BSA must occur on stamping with anti-rabbit antibody when there is specific interaction. This is indeed the case. The other four antigen spots exhibit non-specific transfer (cf. FIG. 19). Comparison of the non-specific transfers shows that these are approximately of equal proportions, regardless of the probe that was used. This is an indication that the order of magnitude of the non-specific transfer is conditioned by the actual experimental arrangement, and that the specific transfers fluctuate according to the protein involved. Hence, a much higher transfer can be achieved, for example with the polyclonal antibodies used here as analyte, than with the monoclonal antibodies.

EXAMPLE 7

Sample Complex: Antibody-antigen: Sensor Complex: DNA-DNA (Detection of Antigen)

The aim is to detect an antigen specifically and in parallel on four spots. The receptor molecules are represented by an antibody that recognizes the antigen. The antibody is bound covalently to the support member. The associated probe is represented by complexes comprising DNA and a second biotinylated antibody directed against the antigen. The binding between said biotinylated antibody and the DNA is realized with biotinylated DNA and Streptavidin. The sensor complex used is in the form of two DNA molecules hybridized in the manner of a zip fastener. The first binding partner of the sensor complex is a DNA molecule, the 5' end of which is bound via an amino group to the stamp member. The second binding partner of the sensor complex is a fluorescence-marked DNA molecule, to the 3' end of which biotin is bound. This biotin enables linkage with Streptavidin and hence the binding with the biotinylated antibody (cf. FIG. 21).

The probes are located on the stamp member in a mirror of the receptor slots on the support member in such a way that, when the surfaces are in contact, the spots with the probes are always positioned opposite the spots with the associated receptors. If an analyte has bound to a receptor molecule, the associated probe can bind to the analyte in the contact phase. If a tensile force is then applied to the bindings thus formed when separating the stamp member and the support member, the weakest binding must be broken. Since the sensor complex hybridized in zip-like manner has a lower stability when a tensile force is applied to the entire conjugate than the other bindings in the conjugate, namely Streptavidin-biotin bindings, antigen-antibody interaction as well as the covalent binding of the antibody to the support member, the sensor complex opens when the surfaces are separated and the fluorescence-marked probe remains bound to the analyte.

Stamp Construction:

A microstructured stamp member made of PDMS (polydimethyl siloxane) was fabricated. The structures consisted of stamp member feet measuring approx. 100×100 μm, separated by wells approx. 25 μm wide and 1 μm. To this end, a mixture comprising a 1:10 mixture of wetting reagent and silicone elastomer (Sylgard 184, Dow Corning) was poured between an appropriately structured silicon wafer and a smooth Plexiglas plate after repeated degassing and incubated for 24 h at room temperature. After polymerization, the structured surface of the stamp member was exposed to an $H_2O$ plasma at 2 mbar in a plasma oven for 60 s.

Coating the Stamp Member:

The oxidized surface was incubated with a solution comprising 2% aminopropyidimethylethoxysilane (ABCR, Karlsruhe, Germany) in 10% $H_2O$ and 88% ethanol for 30 min. The silanized surface was rinsed with ethanol and ultrapure water, then dried in a stream of nitrogen gas. A bifunctional PEG derivative, one end of which had an amino-reactive NHS group (N-hydroxy-succinimide) and the other end a carboxy group, was linked to the amino groups of the silane. 25 μl of a 20 mM NHS-PEG-COOH solution (Shearwater, Huntsville, USA) (in $H_2O$) were incubated under a round cover glass 12 mm in diameter for 2 h in a moist atmosphere at room temperature. It was rinsed with ultrapure water and dried in a stream of nitrogen gas. Surface amino groups that had not yet reacted were blocked using with a 6 mM solution (in $H_2O$) of NHS-PEG-methoxy (Rapp Polymere, Tübingen, Germany). This was done by incubating 25 μl of the solution for 1 h under a round cover glass.

Once the latter step has been carried out, a surface with carboxy groups for coupling with the first reference complex oligo is available. To this end, the first reference complex oligo (sequence: see Example 4) was mixed with an aqueous EDC solution (1-ethyl-3-(3-dimethylamino-propyl)carbiimide; Sigma, Taufkirchen, Germany). The final concentration of oligo was 25 μM, and the EDC concentration was 50 mM. The freshly mixed solution was spotted (in 5×1 μl spots) onto the surface and incubated for 2 h at room temperature. The surface was then rinsed with 1×SSC+0.5% SDS for 2×30 min and blocked overnight with 1% by weight bovine serum albumin (BSA) at 4° C. To finish, the surface was rinsed with water and dried in a stream of nitrogen gas.

Structure of Probe:

To hybridize the unzip oligo with biotin (sequence: see Example 4), a 2 µM solution in 5×SSC was prepared. 10 µl of this hybridization solution were incubated under a round cover glass (12 mm in diameter) for 1 h at room temperature in a moist atmosphere. It was washed for 3×5 min with 1×SSC+0.1% SDS, rinsed with ultrapure water and dried in a stream of nitrogen gas.

To bind the Streptavidin (Sigma, Taufkirchen, Germany), 60 µl of a Streptavidin solution was pipetted onto a PDMS piece. The concentration of Streptavidin solution was 20 µg/ml in PBS+0.2% BSA. The PDMS pieces were incubated at room temperature for 45 min and subsequently washed with PBS+0.05% Tween 20.

The biotinylated antibody was an antibody directed against His tags (Dianova, Hamburg). This antibody was diluted to 20 µg/ml in PBS+0.2% BSA. The PDMS pieces were incubated with 60 µl of this solution for 1 h, washed with PBS+0.05% Tween, rinsed with water and dried in a stream of nitrogen gas.

Coating the Support Member:

Glass slides coated with aldehyde silane (CSS type, Genpak, Brighton, UK) were used as the support member. A bifunctional PEG, one end of which had an amino group and the other end a carboxy group, was linked to the aldehyde groups of the silane. 200 µl of a 6 mM NHS-PEG-COOH solution (Shearwater, Huntsville, USA) (in $H_2O$) were incubated under a round, 24×60 $mm^2$ cover glass for 2 h in a moist atmosphere at room temperature. It was rinsed with ultrapure water and dried in a stream of nitrogen gas. The Schiffs bases were then reduced for 30 minutes with 1% by weight sodium borhydride in $H_2O$.

Once the latter step has been carried out, a surface with carboxy groups for coupling the antibodies is available. This was done by activating the carboxy groups with EDC and NHS (N-hydroxy-succinimide; Sigma, Taufkirchen, Germany) over the whole surface. The surface was incubated with a freshly prepared solution (200 µl) of 50 mM EDC and 50 mM NHS under a 24×60 $mm^2$ cover glass for 30 min in a moist atmosphere at room temperature. It was then rinsed with water and dried in a stream of nitrogen gas.

Immobilization of the Antibody:

An antibody against protein p53 (Klon Pab421, Calbiochem, Darmstadt) was diluted, beginning with the parent solution to a final concentration of 100 µg/ml in 2 Vol.-% glycerine.

The spot solution of the antibody was manually pipetted as 1 µl spots (altogether 4 spots) onto the support member. The spots were incubated on the surface for 1 h at room temperature and washed off with PBS. The activated carboxy groups remaining in addition to the spots were blocked overnight with 1% by weight BSA in PBS. To finish, the surface was washed with PBS+0.05% Tween 20.

Binding the Analyte (Recombinant p53 with His-Tag) from Rabbit Serum:

The antigen (p53-His, positive control for anti-His antibody, Dianova, Hamburg) was diluted in rabbit serum to a concentration of 2 µg/ml. 40 µl of this solution were incubated on the spots for 1 h at room temperature. After incubation, the slides were washed in PBS+0.05% Tween, rinsed with water and dried in a stream of nitrogen gas.

Spotting:

The surfaces were brought closer together under PBS that the probes spotted on the stamp member could come into contact and interact with the analytes on the support member. After incubation for 30 minutes, the surfaces were separated from each other.

Scan:

The support member was scanned with a laser scanner for the fluorescence-marked transferring probe.

Analysis and Conclusions:

In order to be able to show the specificity of transfer, the spots were arranged on the stamp member and support member according to the following scheme:

| Stamp | | Support material: | |
|---|---|---|---|
| anti-His | anti-His | anti-p53/ p53-His | anti-p53/ p53-His |
| anti-His | | | |
| anti-His | anti-His | anti-p53/ p53-His | anti-p53/ p53-His |

After spotting, four spots of the probe can interact in this arrangement with the antigen that has been bound by the anti-p53 antibody. The middle spot on the probe, in contrast, has contact only with the passivation of the support member. If transfer of the fluorophore of the probe to the support member is due to a specific interaction, transfer to the antigens must be significantly higher than transfer to the passivation.

This was confirmed in the experiment described above, in which four parallel spotting tests were carried out. A fluorescence scan is shown in FIG. 22. For one spotting test, the mean value (four spots) of the computed intensities (see Example 6) for transfer to the antigens was 4624±409. For this test, transfer to the passivation is 673. Accordingly, the specific transfer is higher than the non-specific transfer by a factor of seven. The mean value for the ratio of specific to non-specific transfer is 7.2±2.1 for the four tests that were conducted.

The invention claimed is:

1. A method for determining an analyte in a sample, the method comprising:
   contacting a sample that might contain the analyte being determined with a first surface so that the analyte possibly contained in the sample is bound to the first surface;
   bringing a second surface to which a probe that can bind the analyte is bound close to the first surface-so that a probe comprising a marker and the analyte can interact, the binding of the probe to the analyte and the binding of the analyte to the first surface being more stable under an externally applied tensile force than the binding of the probe to the second surface;
   separating the second surface and the first surface from each other; and
   determining whether the probe comprising a marker is bound to the first surface and/or how much probe is bound to the second surface.

2. The method according to claim 1, characterized in that a receptor that can bind the analyte is immobilized on the first surface, the binding of the analyte to the receptor being more stable under the externally applied tensile force than the binding of the probe to the second surface.

3. The method according to claim 2, characterized in that the receptors and/or probes are selected from the group consisting of: polyclonal antibodies, monoclonal antibodies, antibody fragments, and antibody derivatives that can recognize and bind the analyte.

4. The method according to claim 3, characterized in that the receptors and/or probes used are antibody fragments or derivatives selected from the group consisting of: Fv-, Fab-, Fab'- or F(ab')$_2$ fragments, single-chain antibody fragments, bispecific antibodies, chimenc antibodies, humanized antibodies and fragments containing complementarity determining regions that recognize an epitope of the analyte.

5. The method according to claim 1 or claim 2, characterized in that the receptors and/or probes are selected from the group consisting of: nucleic acids, synthetic nucleic acids, and three-dimensional structures thereof.

6. The method according to any of claims 1-4, characterized in that the analyte is selected from the group consisting of: proteins, polypeptides, peptides, nucleic acids, modified nucleic acids, peptide nucleic acids, locked nucleic acids, three-dimensional nucleic acid structures, aptamers, carbohydrates, and modified variants thereof.

7. The method according to claim 6, characterized in that the analyte is a protein, polypeptide or a peptide.

8. The method according to any of claims 1-4, characterized in that the probe binds specifically to the analyte.

9. The method according to any of claims 1-4, characterized in that the probe is selected from the group consisting of: antibodies, antibody fragments and antibody derivatives.

10. The method according to claim 1, characterized in that the probe is immobilized at the second surface by a sensor complex.

11. The method according to claim 10, characterized in that the sensor complex comprises a first binding partner that is bound to the second surface and a second binding partner that is bound fixedly to the probe, wherein the first binding partner and the second binding partner can bind non-covalently to each other.

12. The method according to claim 10, characterized in that the first binding partner and the second binding partner are nucleic acids.

13. The method according to claim 12, characterized in that the first binding partner and the second binding partner are selected from the group consisting of: single-stranded DNA, single-stranded RNA, and combinations thereof.

14. The method according to claim 13, characterized in that the 5' end of the first binding partner is bound to the second surface and the 3' end of the second binding partner is bound to the probe, or that the 3' end of the first binding partner is bound to the second surface and the 5' end of the second binding partner is bound to the probe.

15. The method according to any of claims 1-4 or 10-14, characterized in that the second surface comprises a plurality of areas separated from each other, in which probes with different specificity for different analytes are bound.

16. The method according to any of claims 2-4 or 10-14, characterized in that the support member comprises a plurality of areas separated from each other, in which receptors with different specificity for different analytes are bound.

17. The method according to claim 15, characterized in that the first surface has a plurality of areas separated from each other, in which receptors with different specificity for different analytes are bound in such a way that they are disposed symmetrically to the areas on the second surface, so that when the second surface and the support member approach each other, the areas on the probes and receptors that have specificity for the same analyte become aligned.

18. The method according to claim 15, characterized in that both the first surface and the second surface have areas in which receptors are immobilized, as well as areas in which probes are immobilized, the respective areas being so arranged that when the second surface and the first surface are brought into contact, areas with receptors for an analyte and areas with probes for the same analyte are positioned facing each other.

19. The method according to any of claims 1-4 or 10-14, characterized in that the second surface and/or first surface have sub-areas on which a plurality of spots are arranged.

20. The method according to claim 19, characterized in that the second surface and/or first surface-have sub-areas with a plurality of spots, the spots on a sub-area each having different receptors or probes that can bind to an analyte.

21. The method according to claim 19, characterized in that the second surface and/or the first surface-have at least one spot where receptors capable of binding directly with the probe are immobilized, said spots being used to monitor coupling.

* * * * *